United States Patent [19]
Sanders et al.

[11] Patent Number: 5,900,109
[45] Date of Patent: May 4, 1999

[54] METHOD AND APPARATUS FOR SEALING ABSORBENT MATERIALS IN AN ABSORBENT PRODUCT

[75] Inventors: Donald Joseph Sanders, Larsen; Mark Charles Jacobs, Appleton; Lisette Marie Curtin, Neenah; Keith Gervaise Bellin, Green Bay; Rob David Everett, Neenah; Lee Patrick Garvey, Little Chute, all of Wis.

[73] Assignee: Kimberly-Clark Worldwide, Inc., Neenah, Wis.

[21] Appl. No.: 08/160,460

[22] Filed: Dec. 1, 1993

Related U.S. Application Data

[63] Continuation of application No. 07/978,576, Nov. 19, 1992.

[51] Int. Cl.⁶ ........................................ B32B 31/00
[52] U.S. Cl. ..................... 156/552; 156/361; 156/362; 156/291; 156/517
[58] Field of Search ........................... 156/361, 362, 156/366, 367, 290, 291, 516, 517, 552, 553

[56] References Cited

U.S. PATENT DOCUMENTS

| | | | |
|---|---|---|---|
| 3,068,933 | 12/1962 | Klar | 156/367 |
| 3,295,526 | 1/1967 | Sabee | 128/287 |
| 3,509,881 | 5/1970 | Sabee | 128/287 |
| 3,523,536 | 8/1970 | Ruffo | 128/287 |
| 3,636,952 | 1/1972 | George | 128/287 |
| 3,661,680 | 5/1972 | Gore | 156/467 |
| 3,669,103 | 6/1972 | Harper et al. | 128/156 |
| 3,924,626 | 12/1975 | Lee et al. | 128/287 |
| 3,927,673 | 12/1975 | Taylor | 128/287 |
| 3,984,272 | 10/1976 | Teed | 156/291 X |
| 4,050,462 | 9/1977 | Woon et al. | 128/287 |
| 4,069,822 | 1/1978 | Buell | 128/294 |
| 4,147,580 | 4/1979 | Buell | 156/291 |
| 4,259,958 | 4/1981 | Goodbar | 128/287 |
| 4,261,782 | 4/1981 | Teed | 156/361 |
| 4,325,372 | 4/1982 | Teed | 128/287 |
| 4,557,777 | 12/1985 | Sabee | 156/201 |
| 4,573,986 | 3/1986 | Minetola et al. | 604/366 |
| 4,666,647 | 5/1987 | Enloe et al. | 264/121 |
| 4,699,823 | 10/1987 | Kellenberger et al. | 428/219 |
| 4,760,764 | 8/1988 | De Jonckheere et al. | 156/259 X |
| 4,761,258 | 8/1988 | Enloe | 264/518 |
| 4,798,603 | 1/1989 | Meyer et al. | 604/378 |
| 4,927,582 | 5/1990 | Bryson | 264/113 |
| 4,950,264 | 8/1990 | Osborn, III | 604/385.1 |
| 4,994,037 | 2/1991 | Bernardin | 604/368 |
| 5,028,224 | 7/1991 | Pieper et al. | 425/80.1 |
| 5,030,314 | 7/1991 | Lang | 156/390 |
| B1 3,860,003 | 4/1989 | Buell | 604/385.2 |

FOREIGN PATENT DOCUMENTS

| | | |
|---|---|---|
| 0217666 | 4/1987 | European Pat. Off. . |
| 0439012 | 7/1991 | European Pat. Off. . |
| 2170108 | 7/1986 | United Kingdom . |

*Primary Examiner*—James Engel
*Attorney, Agent, or Firm*—Paul Yee

[57] ABSTRACT

A method and apparatus for enveloping a series of absorbent cores with a fluid-permeable layer includes a first web supplying mechanism for providing a first layer of fluid-permeable material, and a depositing mechanism for positioning a series of absorbent cores on the first layer. Each of the absorbent cores defines a periphery thereof and includes superabsorbent material therein. A second web supplying means provides a second layer of fluid-permeable material to sandwich the absorbent cores between the first and second layers. A sealing mechanism secures the first layer to the second layer along an attachment region thereof which is located adjacent to at least a pair of side edge regions of the absorbent cores. The attachment region is constructed to substantially prevent movement of superabsorbent material from the absorbent cores through the attachment region. A separating mechanism removes selected regions of the first and second layers which are located adjacent to the attachment region and are spaced from the absorbent cores.

23 Claims, 17 Drawing Sheets

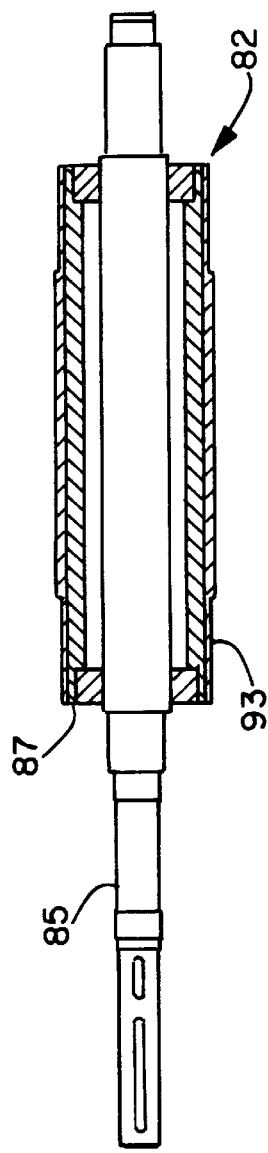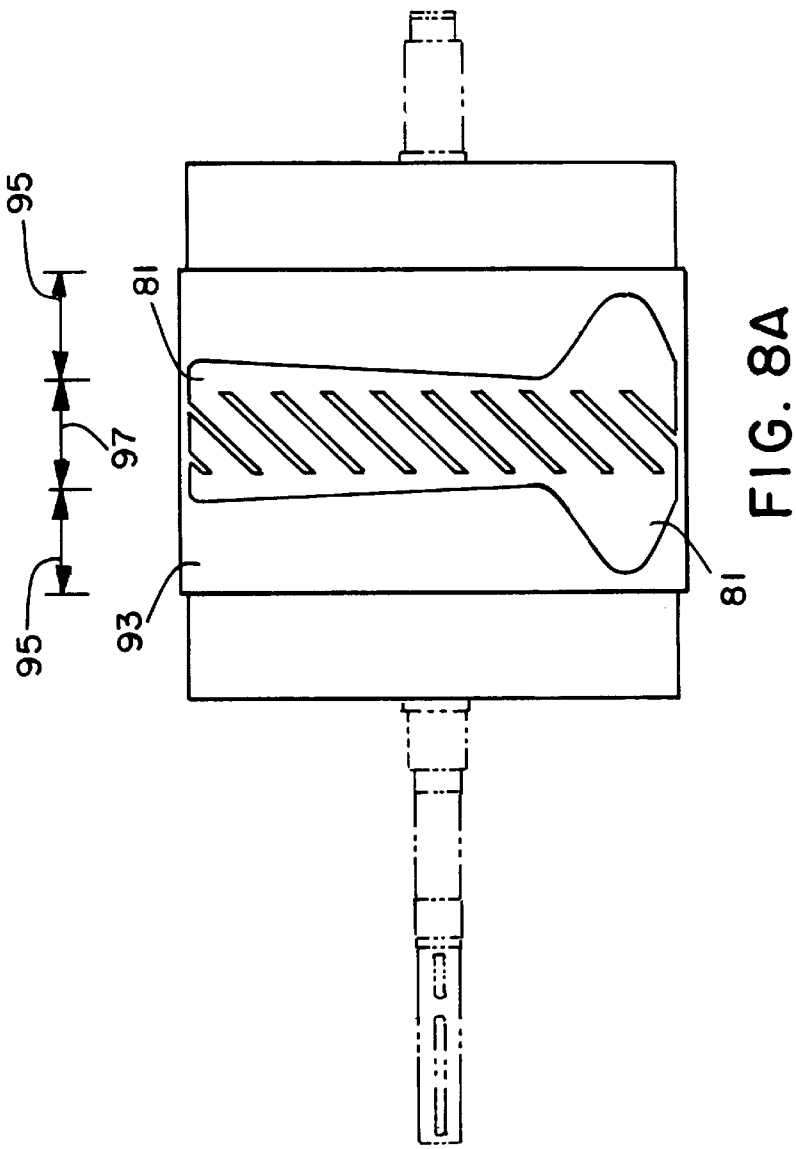

METHOD AND APPARATUS FOR SEALING ABSORBENT MATERIALS IN AN ABSORBENT PRODUCT

This is a continuation of copending application Ser. No. 07/978,576 filed on Nov. 19, 1992.

FIELD OF THE INVENTION

The present invention relates to a method and apparatus for holding and containing selected absorbent materials within an absorbent pad. More particularly, the present invention relates to a method and apparatus for enveloping an absorbent core with a fluid-permeable layer to provide an absorbent body suitable for use in disposable, personal care articles, such as disposable diapers, feminine care products, incontinence garments or the like.

BACKGROUND OF THE INVENTION

Conventional absorbent articles have included an absorbent core which is composed of woodpulp fluff and is sandwiched between and bonded to an outer cover layer and a liquid permeable facing sheet layer. The bonding may comprise strips of hot melt or pressure sensitive adhesive, overall or patterned heat sealing, a printed pattern of adhesives, or the like. For example, see U.S. Pat. No. 4,050,462 to Woon et al. Attachment of the absorbent core to a facing layer of tissue with sprayed adhesive is described in U.S. Pat. No. 3,523,536 to Ruffo. The absorbent core may include particles of superabsorbent material. For example, see U.S. Pat. No. 3,669,103 to Harper et al. and U.S. Pat. No. 4,699,823 to Kellenberger et al. In addition, the absorbent structures may include one or more layers of tissue wrap material. Such tissue wraps are, for example, described in U.S. Pat. No. 3,924,626 to Lee et al. and U.S. Pat. No. 4,798,603 to Meyer et al.

Conventional tissue wrap arrangements for absorbent cores have, however, not provided an adequate seal about the periphery of the absorbent core when the absorbent core includes relatively large amounts of superabsorbent material. As a result, excessive amounts of superabsorbent particles may migrate from the absorbent core and move to undesired locations within the absorbent article. If the superabsorbent material moves to a location against the outer cover, the dry particles may perforate the outer cover and the wetted particles may create an unsightly, slimy feeling gel against the outer cover. If the superabsorbent material moves to the liner layer of the article, the wetted superabsorbent may produce a undesired gel against the wearer's skin. As a result, there has remained a need for an apparatus and method for producing an absorbent article having an improved tissue wrap structure about an absorbent core.

BRIEF DESCRIPTION OF THE INVENTION

The present invention provides a distinctive apparatus for enveloping an absorbent core with a fluid-permeable layer. Generally stated, the apparatus comprises a first web supplying means for providing a first layer of fluid-permeable material, and a depositing means for positioning a series of absorbent cores on the first layer. Each of the absorbent core defines a periphery thereof and includes superabsorbent material therein. A second web supplying means provides a second layer of fluid-permeable material to sandwich the absorbent core between the first and second layers of material. Sealing means secure the first layer to the second layer along an attachment region thereof which is located adjacent to at least a pair of side edge regions of the absorbent core. The attachment region is constructed to substantially prevent movement of superabsorbent material from the absorbent core through the attachment region. Separating means remove selected regions of the first and second layers which are located adjacent to the attachment region and are spaced from the absorbent core.

In a method aspect of the invention, a distinctive process for enveloping an absorbent core with a fluid-permeable layer comprises the steps of supplying a first layer of fluid permeable web material, and positioning a series of absorbent cores on the first layer. Each of the absorbent core defines a periphery thereof and includes superabsorbent material therein. A separate, second layer of fluid permeable web material is supplied to sandwich the absorbent core between the first and second layers of material. The first layer is secured to the second layer along a selected attachment region thereof which is located adjacent to at least a pair of side edge regions of the absorbent core. The attachment region is constructed to substantially prevent movement of superabsorbent material from the cores through the attachment region. Selected regions of the first and second layers are removed, and the selected regions are spaced from the absorbent core and located adjacent to the attachment region.

The apparatus and method of the invention can advantageously construct an absorbent structure which is better able to contain superabsorbent particles therein. The invention can be incorporated into a high speed manufacturing operation to more effectively seal the side edge sections and end edge sections of a tissue wrap. In addition, particular aspects of the invention can incorporate components which are configured to more accurately position the sealed sections about the periphery of an absorbent core. Other aspects of the invention can advantageously envelope an absorbent core with a fluid-permeable layer having different characteristics at predetermined locations thereof. As a result, a portion of the absorbent core can be covered with one type of fluid-permeable layer and another portion of the absorbent core may be covered with a different type of fluid-permeable layer. The different types of fluid-permeable layers can facilitate the production of the absorbent structure and can help improve the performance of the final absorbent article.

BRIEF DESCRIPTION OF THE DRAWINGS

The invention will be more fully understood and further advantages will become apparent when reference is made to the following detailed description of the invention and the drawings in which:

FIG. 8 representatively shows cross-sectional view of a patterned impression roll employed with the technique of the invention;

FIG. 8A representatively shows an unrolled, flat view of the outer surface of the patterned impression roll of FIG. 8;

FIG. 15A representatively shows a side elevational view of the thermal bonding rolls illustrated in FIG. 15;

FIG. 15B representatively shows a top view of the of thermal bonding rolls of FIG. 15.

DETAILED DESCRIPTION OF THE INVENTION

The apparatus and method of the present invention will be described in the context of producing a disposable diaper. It should be readily appreciated, however, that the technique of the invention may be employed to manufacture other types of disposable articles, such as feminine care products, incontinence garments and the like.

Figure 1:
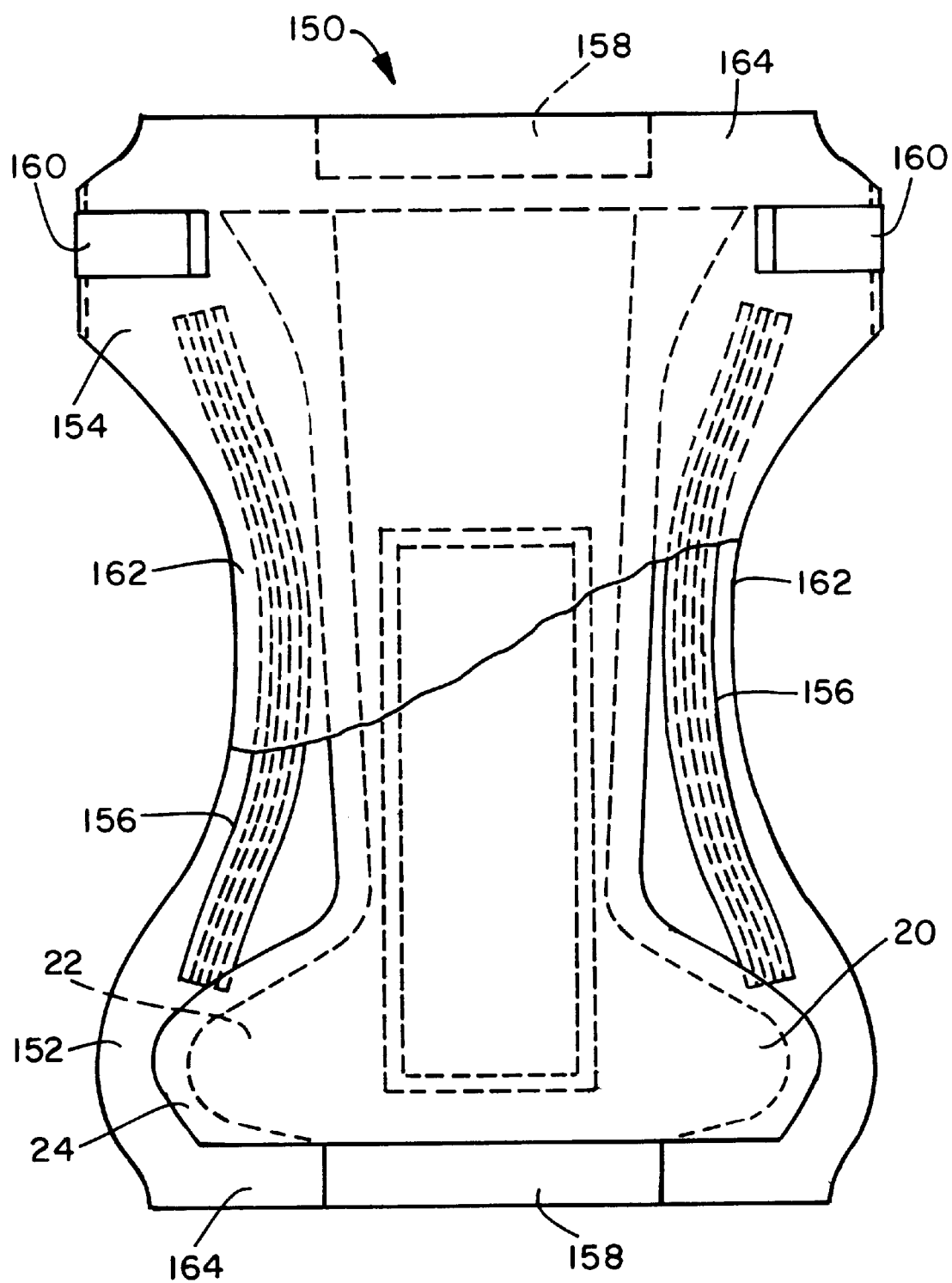
FIG. 1 shows a partially cut-away, top plan view of a representative absorbent article which can be produced while employing the apparatus and method of the invention.

Absorbent articles, such as disposable diapers, have included an absorbent body composed of an absorbent core and one or more wrapping layers, such as one or more layers of high, wet-strength cellulosic tissue. As illustrated in FIG. 1, a representative diaper article 150 is shown in its fully extended state with all elastic gathering stretched out. The diaper includes a backsheet layer 152, a topsheet layer 154 positioned in an adjacent facing relation with the backsheet layer, and an absorbent body 20 sandwiched between the backsheet and topsheet layers. Typically, the topsheet and backsheet layers are constructed to extend past the terminal edges of the absorbent body to provide laterally spaced, side margins 162 and longitudinally spaced, end margins 164. Leg elastics 156 can be attached to each of the side margins to provide elasticized leg gathers, and waist elastics 158 can be attached to either or both of the end margins to provide elasticized waist gathers. A fastening means, such as adhesive tapes 160, are anchored to opposed sides of at least one longitudinal end of the diaper, and are appointed to adhere to the opposite longitudinal end of the diaper to thereby secure the diaper on a wearer. A more detailed description of a representative disposable diaper is, for example, shown in U.S. patent application Ser. No. 07/757,760 "Thin Absorbent Article Having Rapid Uptake of Liquid", Hanson et al., filed Sep. 11, 1991 (Attorney Docket No. 9922), the disclosure of which is hereby incorporated by reference to the extent that it is consistent herewith.

Figures 2, 2A, 2B:
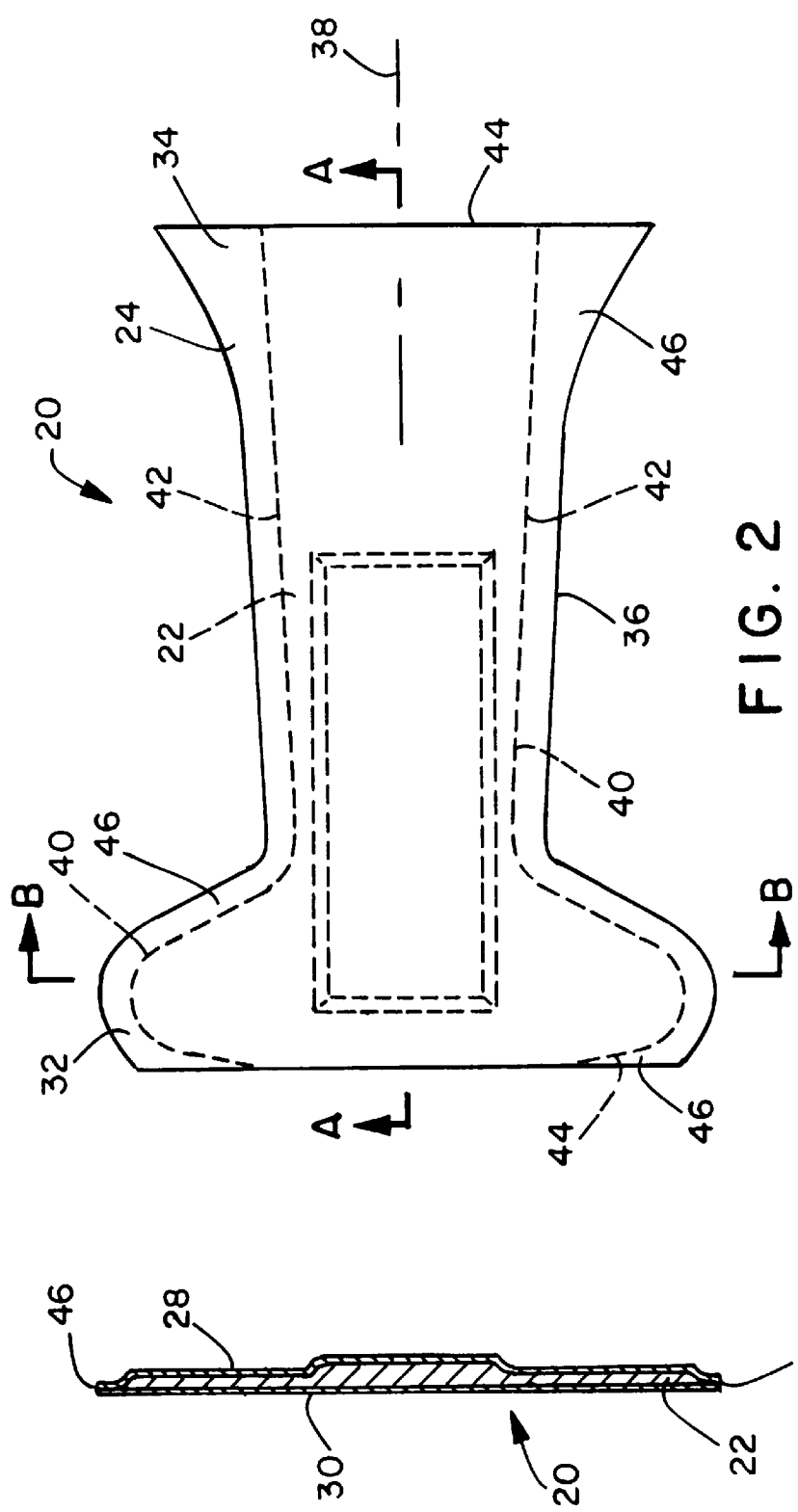
FIG. 2 representatively shows a top plan view of an absorbent core produced with the apparatus and method of the invention.
FIG. 2A representatively shows a cross-sectional view taken along section A—A of FIG. 2.
FIG. 2B representatively shows a cross-sectional view taken along section B—B of FIG. 2.

With reference to FIG. 2, absorbent body 20 comprises an absorbent core 22 which includes a mass of substantially hydrophilic fibers, such as cellulosic wood pulp fibers commonly referred to as wood pulp fluff. The absorbent core may also include other natural fibers, synthetic fibers or combinations thereof. Such fibers may be naturally hydrophilic, or may be composed of hydrophobic material which has been coated or otherwise treated to render it sufficiently hydrophilic. Absorbent body 20 can further include superabsorbent material 26. In the illustrated embodiment, the absorbent body includes hydrophilic fibers composed of cellulosic wood pulp fluff, and superabsorbent particles composed of a polyacrylate superabsorbent material. In particular aspects of the invention, absorbent core 22 includes about 30–70 wt % (weight percent) superabsorbent material. Alternatively, the absorbent core may include about 40–60 wt % of superabsorbent material and may optionally include 45–55 wt % of superabsorbent particles to provide selected levels of performance.

The absorbent core may have any desired contoured shape. For example, the absorbent core may be hourglass, I-shaped, T-shaped, or the like. In the illustrated embodiment, the absorbent core has a modified T-shape, and defines a front waistband section 32, a rear waistband section 34 and an intermediate section 36 which interconnects the front and rear waistband sections. The absorbent core also includes a longitudinal centerline 38 and a core periphery 40. The core periphery includes laterally spaced, side edges 42 and longitudinally spaced, end edges 44. The edges of the core periphery, particularly the core side edges, are curved or otherwise non-rectilinear and include a predetermined arrangement of one or more generally concave and/or convex sections.

To help maintain the integrity of absorbent core 22, absorbent body 20 can include one or more layers of a fluid permeable wrap material 24. Such fluid permeable material is permeable to either gas or liquid. In particular embodiments at least an operative portion of wrap material 24 is permeable to gas, and in other embodiments the operative portion of wrap material 24 is permeable to gas and liquid. For example, wrap material 24 can be a cellulosic tissue or other liquid-permeable nonwoven fabric placed in a facing, adjacent relation with absorbent core 22.

Laterally extending side portions of wrap 24 have ordinarily been folded over and around the side edges of the absorbent core to overlap on a top or bottom major surface of the core. The resultant wrap layer 24 has generally been rectangular in shape, and when absorbent core 22 includes a contoured, non-rectangular or non-linear periphery, the edges of the wrap layer have not conformed to the peripheral contours of the shaped absorbent core. As a result, it has been desireable to cut away and remove selected, excess portions of the folded-over, lateral side regions of the wrap material. In addition, when an individual absorbent core 22 is separated from a manufactured, interconnected plurality of absorbent cores, the longitudinal end regions of wrap 24 may also be cut. The various cut edges of wrap 24 can effectively define a top wrap layer and a bottom wrap layer which are separated from each other by the thickness of absorbent core 22. As a result, constituent materials within the core, such as particles of superabsorbent material, may migrate through the separation and out of the core in excessive amounts.

To more effectively contain constituent materials within absorbent core 22, fluid permeable wrap layer 24 is distinctively constructed to include a substantially sealed attachment region 46 which interconnects the top and bottom sections of the wrap layer to each other. The attachment region extends at least along side edges 42 of core 22, and preferably, also extends along end edges 44 of the core. In particular arrangements, the attachment region can substantially surround the core perimeter.

The shown embodiment of wrap layer 24 includes a bottom wrapsheet layer 30 and a top wrapsheet layer 28. Bottom wrapsheet layer 30 is typically positioned adjacent to an appointed outer side of absorbent core 22, and is typically sandwiched between the absorbent core and a substantially liquid impermeable outer cover component of the finished absorbent article.

Top wrapsheet layer 28 is typically positioned against an appointed bodyside of absorbent core 22, and may be composed of a material which is the same as or different than the material employed to construct bottom wrapsheet layer 30. In the shown embodiment, for example, a fibrous top wrapsheet layer 28 is a separately provided, fluid permeable layer which has a relatively lower porosity value than bottom wrapsheet layer 30.

The top and bottom wrapsheet layers cover a larger area than absorbent core 22, and extend beyond the peripheral edges of the absorbent core along marginal regions of wrapsheet layers 28 and 30. The marginal regions of the wrapsheet layers connect to each other along a flange-like attachment region 46 which protrudes away from the absorbent core. The interconnection between top wrapsheet 28 and bottom wrapsheet 30 along attachment region 46 is created with a suitable securing mechanism, such as thermal bonding, adhesive bonding or the like. The securement between the top and bottom wrapsheet layers may be substantially continuous or may be configured in a selected, substantially closed attachment pattern. The substantially closed attachment pattern is configured to sufficiently block movement of SAM particles out of absorbent core 22 through attachment region 46. The closed attachment pattern may leave regions of the top and bottom wrapsheets that are unattached to each other, and the unattached regions may provide limited pathways from the absorbent core through the attachment region. The pathways, however, are sufficiently small and/or circuitous to substantially block the passage of superabsorbent particles. In particular aspects of the invention, the size of the pathways is not more than about 85 times the average size of the superabsorbent particles. Alternatively, the size of the pathways is not more than about 10 times the average size of the superabsorbent particles, and optionally, the size of the pathways is not more than about 7 times the average size of the superabsorbent particles.

Figure 3:
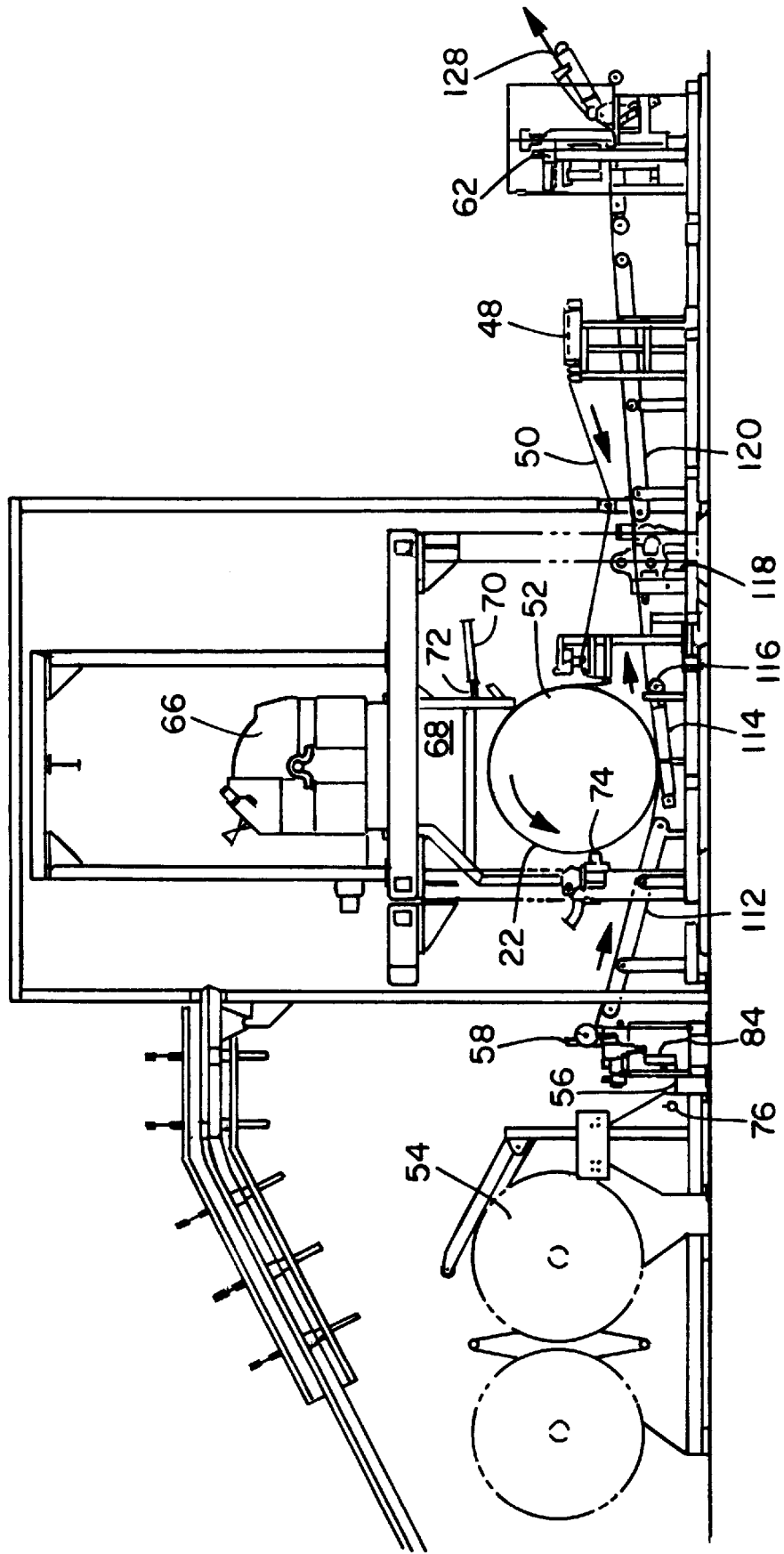
FIG. 3 representatively shows a schematic, side elevational view of the technique of the invention.

With reference to FIG. 3, an apparatus for enveloping a series of absorbent cores 22 with a fluid-permeable layer comprises a first web supplying means which includes a mechanism 48 for providing a first layer of fluid permeable material, such as forming tissue 50. A depositing means, such as forming drum 52 positions the series of absorbent cores onto a first layer 50, and each absorbent core defines a periphery thereof and includes superabsorbent material therein. A second web supplying means, such as second supply roll 54 provides a second layer of fluid permeable material, such as barrier tissue 56, to sandwich the absorbent cores 22 between the first fluid permeable layer 50 and the second fluid permeable layer 56. A sealing means, such as adhesive module 58 secures first layer 50 to second layer 56 along an attachment region 60 (FIG. 9) thereof which is located adjacent to at least a pair of side edge regions 42 of the absorbent cores 22. Attachment region 60 is constructed to substantially prevent movement of superabsorbent material from the absorbent cores 22 through attachment region 60. A separating means, such as cutting mechanism 62, removes selected regions of the first layer 50 and the second layer 56 which are located adjacent to attachment region 60 and are spaced from the absorbent cores 22. A particular aspect of the invention includes a controlling means for regulating a selected registration between attachment region 60 and absorbent cores 22.

The first layer of fluid-permeable material 50 can be continuously supplied from supply roll 48, and a series of conveyor rollers including roller 64 can then be employed to transport and direct the first fluid-permeable layer into the depositing means of the invention. The first layer can be a woven or nonwoven fibrous web (fabric) composed of natural or synthetic fibers, and a nonwoven fabric may be airlaid or wet-laid. Airlaid fabrics include, for example spunbonded fabrics, meltblown fabrics and combinations thereof. In the shown embodiment, the first layer is a liquid-permeable forming tissue 50 composed of a web of high wet-strength cellulosic tissue. The shown embodiment of the tissue has a basis weight within the range of about 15–50 gsm (grams per square meter) and has a density within the range of 0.05–0.15 g/cc. In addition, the fluid permeable first layer can have an air porosity value within the range of about 250–350 cfm/sf (cubic feet per minute per square foot). This relatively high air porosity value can facilitate the formation of air laid fibrous batts directly onto forming tissue 50.

The shown embodiment of the invention air-lays fibrous absorbent material directly onto first layer 50, and includes a hammermill fiberizer 66 and a rotatable forming drum 52. Fiberizer 66 disintegrates sheets of wood pulp fiber and introduces the individual fibers into forming chamber 68. In addition, a superabsorbent supplying means, such as provided by supply conduit 70 and nozzle 72, selectively introduces particles of superabsorbent material into forming chamber 68. Quantities of superabsorbent material may be continuously introduced into the forming chamber or individual quantities of superabsorbent material may be intermittently introduced into the forming chamber with a pulsing mechanism. The chosen technique will depend upon the desired distribution of superabsorbent across the area and through the thickness of the absorbent cores. Suitable techniques for selectively introducing particles of superabsorbent material into a forming chamber are described in U.S. Pat. No. 4,927,582 issued May 22, 1990 to Bryson (Attorney Docket No. 7637.1), and U.S. Pat. No. 5,028,224 issued Jul. 2, 1991 to Pieper et al. (Attorney Docket No. 8761), the disclosures of which are hereby incorporated by reference to the extent that they are consistent herewith.

Forming drum 52 includes a mechanism for forming a vacuum therein to draw the wood pulp fibers and superabsorbent particles onto first layer 50. First layer 50 is carried by the peripheral outer surface of rotatable forming drum 52, which moves first layer 50 through forming chamber 68. The peripheral surface of the forming drum includes an air permeable forming screen, and as air is drawn through the screen by the vacuum within forming drum 52 draws the wood pulp fibers and superabsorbent particles onto first layer 50 to generate a series of airlaid absorbent cores which are substantially regularly spaced along the machine direction length of first layer 50. Suitable mechanisms, which can be employed to form a series of discrete absorbent cores, are shown in U.S. Pat. No. 4,666,647 issued May 19, 1987 to Enloe et al. (Attorney Docket No. 6900) and U.S. Pat. No. 4,761,258 issued Aug. 2, 1988 to Enloe (Attorney Docket No. 6999), the disclosures of which are hereby incorporated by reference to the extent that they are consistent herewith.

A scarfing mechanism is located at an exit end of forming chamber 68. The shown scarfing mechanism includes a scarfing drum 74 which is rotatably driven to operably remove excess absorbent material from the individual absorbent cores. The removed material may optionally be recycled back into forming chamber 68.

The resultant absorbent cores 22 are composed of a selected mixture of absorbent hydrophilic fibers and superabsorbent particles. In particular aspects of the invention, the absorbent cores are constructed to contain at least about 30 wt % (weight percent) of superabsorbent material. Preferably, each absorbent core contains not less than about 40 wt % of superabsorbent, and more preferably, contains not less than about 50 wt % of superabsorbent material. In particular aspects of the invention, the absorbent core contains not more than about 80 wt % of superabsorbent, and preferably contains not more than about 70 wt % of superabsorbent material.

Figure 13:
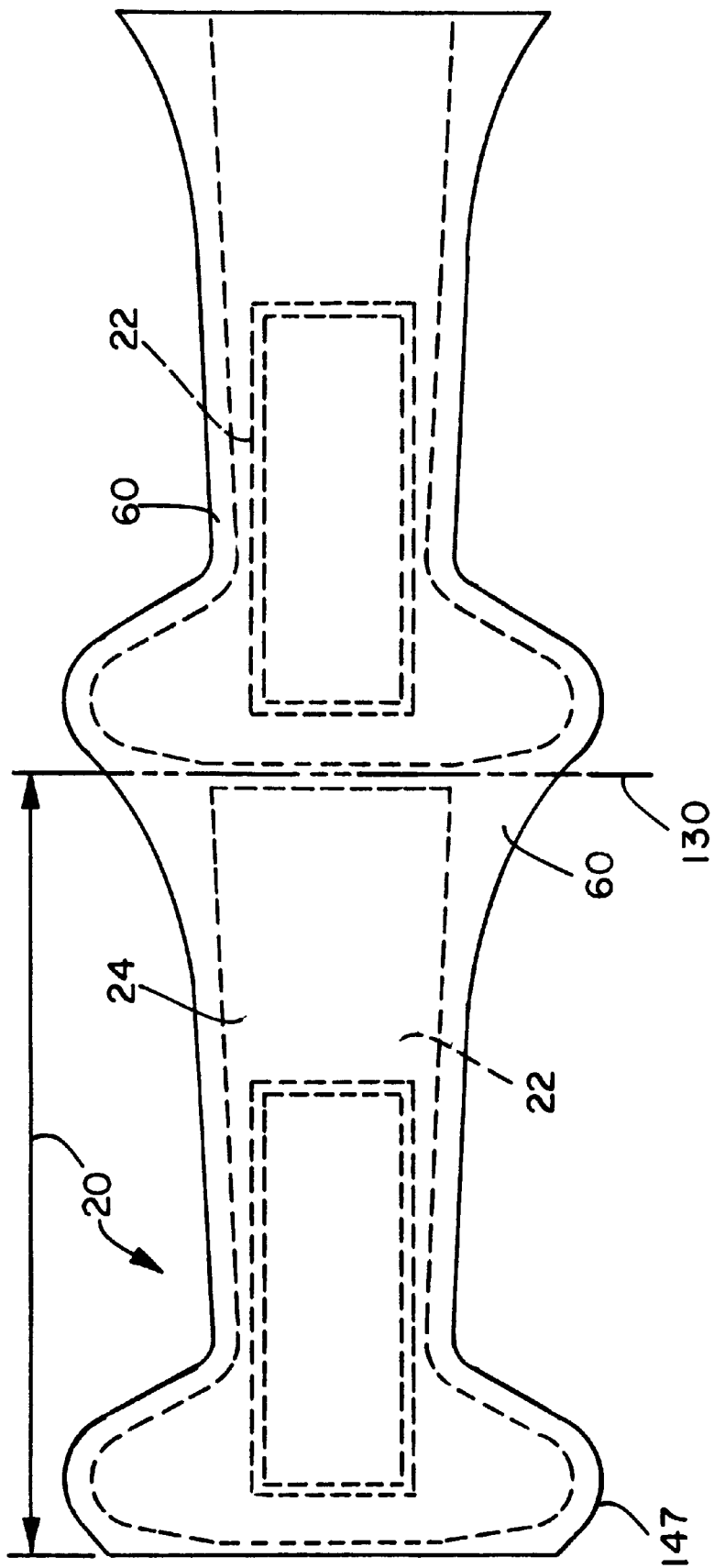
FIG. 13 shows a representative, trimmed composite web suitable for cutting into individual absorbent bodies.

The forming drum or other depositing means can be configured to provide an interconnected series of absorbent cores, or a disconnected series of individual, spatially separated absorbent cores. Where the series of absorbent cores is interconnected, the wrapsheet system can include an attachment region 60 which extends along and adjacent to only the lateral, side edges of each absorbent core. In the illustrated aspects of the invention, the individual adjacent absorbent cores are separated by a discrete distance (e.g. FIG. 13) to better permit the production of a wrapsheet system having an attachment region 60 which extends along and adjacent to substantially the entire edge periphery of each absorbent core. Accordingly, such attachment region may extend along both the side edges and end edges of each absorbent core.

Upon leaving the position of scarfing drum 74, first layer 50 and the series of absorbent cores formed thereon can be removed from forming drum 52 and placed upon a separate, second layer of fluid permeable material 56. The second layer can be a woven or nonwoven fabric composed of natural and/or synthetic fibers, and the nonwoven fabric may be airlaid or wet-laid. Airlaid nonwoven fabrics may include, for example, spunbonded fabrics, meltblown fabrics and combinations thereof. The shown embodiment of second layer 56 is a liquid-permeable layer of barrier tissue composed of cellulosic fibers. The barrier tissue has a basis weight within the range of about 20–30 gsm (grams per square meter), and has a density within the range of about 0.05–0.15 g/cc (grams per cubic cm). In addition, the barrier tissue can have an average pore size value within the range of about 20–60 micrometers. Particular constructions of barrier layer 56 can have an average pore size value within the range of about 20–30 micrometers. Alternative constructions of barrier layer 56 can have an average pore size value within the range of about 40–50 micrometers, and other constructions can have an average pore size value within the range of about 50–60 micrometers.

For the purposes of the present invention, a suitable technique for determining the pore size value of a material can employ a Coulter Porometer, Part No. 9903175. Such a testing device is available from COULTER ELECTRONICS LIMITED, a business having offices located at Luton, England.

Second layer 56 is delivered from a suitable supply roll 54 and transported by suitable conveying rollers 76 and web guide 84 to a suitable attachment bonding module, such as adhesive module 58. Web guide 84 is constructed to control the cross-deckle positioning of barrier tissue 56 within a tolerance range of about 1 inch. A suitable web guide is an electronic edge guiding system available from FIFE CORPORATION, a company having offices in Oklahoma City, Okla. The adhesive module provides a representative mechanism for securing second layer 56 to first layer 50 along an appointed, selectively patterned attachment region 60.

Various types of mechanisms may be employed to form attachment region 60. For example, the attachment region may be formed by adhesive bonding, thermal bonding, sonic bonding or the like. Where adhesive bonding is employed, the adhesive may be applied by patterned extrusion, patterned spraying, patterned printing or the like. The patterns are appropriately configured to substantially avoid placing excessive amounts of adhesive onto the fibrous, hydrophilic material used to construct absorbent cores 22. Excessive amounts of adhesive placed directly onto the surfaces of the absorbent cores may undesirably inhibit the absorbency of the cores and may impart excessive stiffness.

Figure 4:
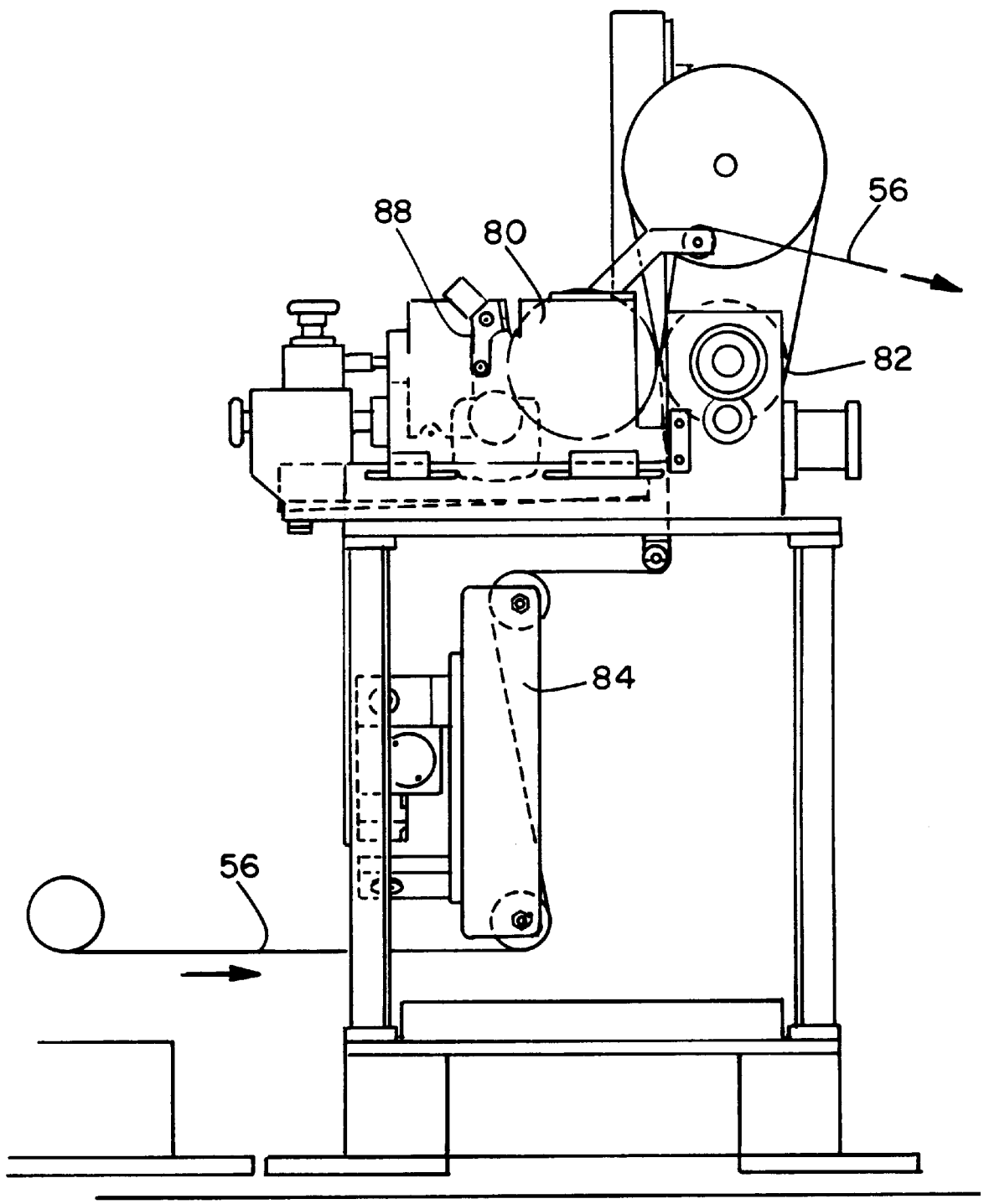
FIG. 4 representatively shows a schematic side view of an adhesive printing module employed with the present invention.

With reference to FIG. 4, the representatively shown embodiment of the invention employs an attachment bonding module which is constructed to print a selected pattern of adhesive onto barrier tissue 56. More particularly, an adhesive printing module 58 employs a rotogravure adhesive printing system, which includes gravure roll 80 and impression roll 82. While the illustrated embodiment employs a rotogravure printing process, it should be appreciated that other printing methods may also be employed to apply the desired patterns of adhesive.

A conveying mechanism which includes conveying rollers 76 and web guide 84 directs the web of barrier tissue 56 into a nip region between the gravure and impression rolls. Rotatable gravure roll 80 has a selected engraved pattern recessed regions formed thereon. An applicating means directs adhesive onto the outer peripheral surface of the gravure roll, and a doctoring device removes excess adhesive from the gravure roll. Impression roll 82 includes a selected pattern of raised areas located on the outer peripheral surface thereof to transfer a selected pattern of adhesive from gravure roll 80 onto the layer of barrier tissue 56 when the barrier tissue is nipped between the gravure and impression rolls.

Various combinations of gravure roll structures and impression roll structures may be employed with the present invention. In one arrangement, the gravure roll has cells engraved over substantially the entire outer cylindrical surface of the gravure roll. The impression roll has a raised pattern formed on its outer cylindrical surface, and the raised pattern corresponds to the pattern of adhesive desired for transfer onto the appointed substrate.

A second arrangement employs a patterned gravure roll upon the surface of which the engraved cells are distributed over a pattern which corresponds to the desired printed pattern of adhesive on the appointed substrate. The nonengraved sections of the gravure roll remain substantially smooth. The smooth areas of the gravure roll are wiped clean of adhesive by doctor blades and only the engraved sections of the gravure roll will hold liquid adhesive. The impression roll has a substantially smooth outer surface. As a result, the adhesive pattern printed onto the appointed substrate substantially corresponds to the overall pattern of cells engraved into the surface of the gravure roll.

A third arrangement, such as that employed by the shown embodiment of the invention, employs both a patterned gravure roll 80 and a patterned impression roll 82. As a result, the amount of adhesive add-on at selected regions can be increased or decreased in accordance with the quantity of liquid adhesive carried by the pattern of engravings formed into the surface of the gravure roll. Different concentrations and volumes of the cells distributed in the selected pattern across the surface of gravure roll 80 can be employed to vary the level of adhesive add-on applied to different areas of the printed pattern. In addition, the raised pattern formed onto the surface of impression roll 82 can determine the discrete areas at which adhesive is transferred onto the appointed substrate.

Figure 5:
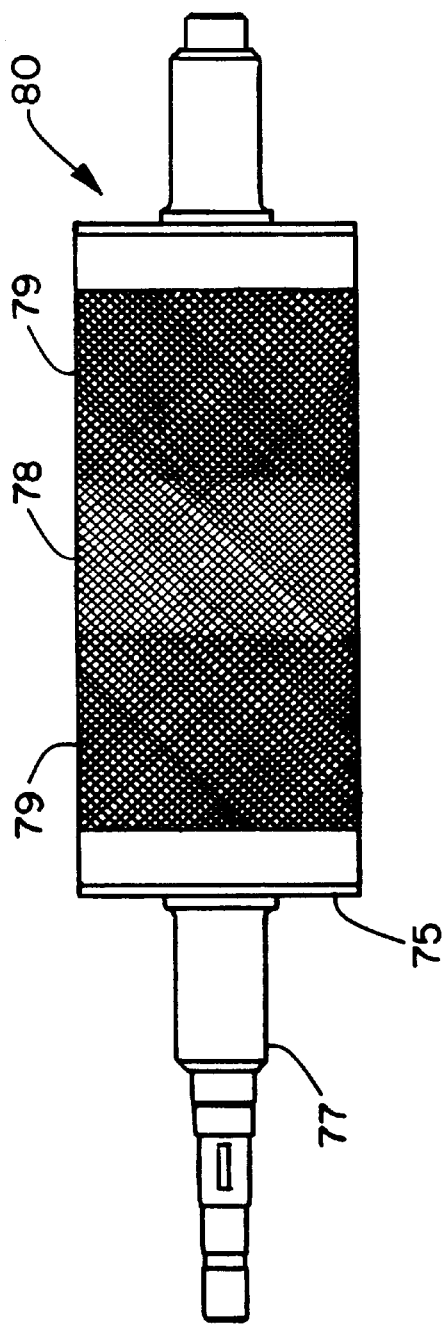
FIG. 5 representatively shows an adhesive printer, gravure roll employed with the technique of the invention.
Figure 5A:
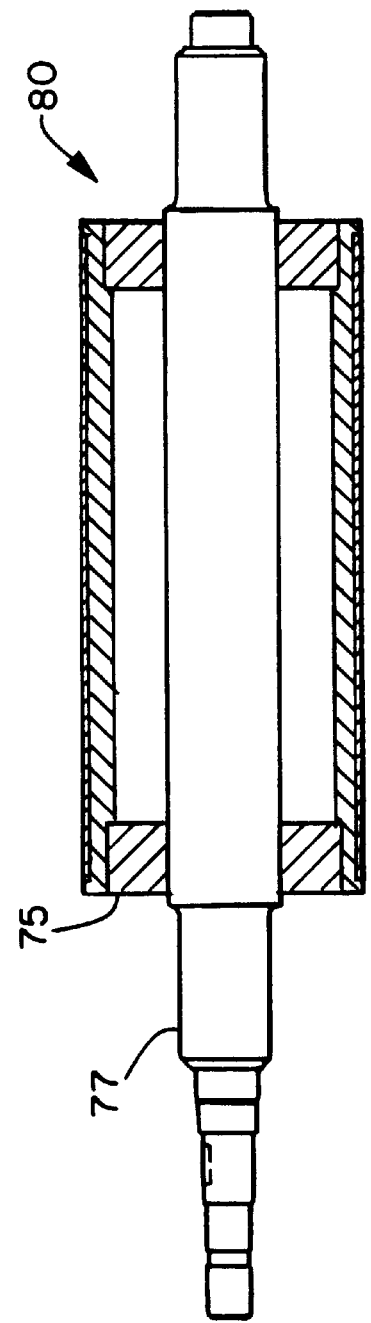
FIG. 5A representatively shows a cross-sectional view of the adhesive printer, gravure roll of FIG. 5.

With reference to FIG. 5, the peripheral, cylindrical surface of gravure roll 80 is constructed of a durable, erosion resistant material, such as hard metal, ceramic or the like, and the peripheral surface is engraved with a predetermined pattern composed of a multiplicity of minute depressions or cells. To form the minute, liquid-bearing cells, the outer peripheral cylindrical surface of gravure roll 80 may be engraved by one or more suitable techniques. Such engraving techniques include, for example, acid etching, mechanical knurling, electronic engraving, laser engraving, or the like.

Figure 6:
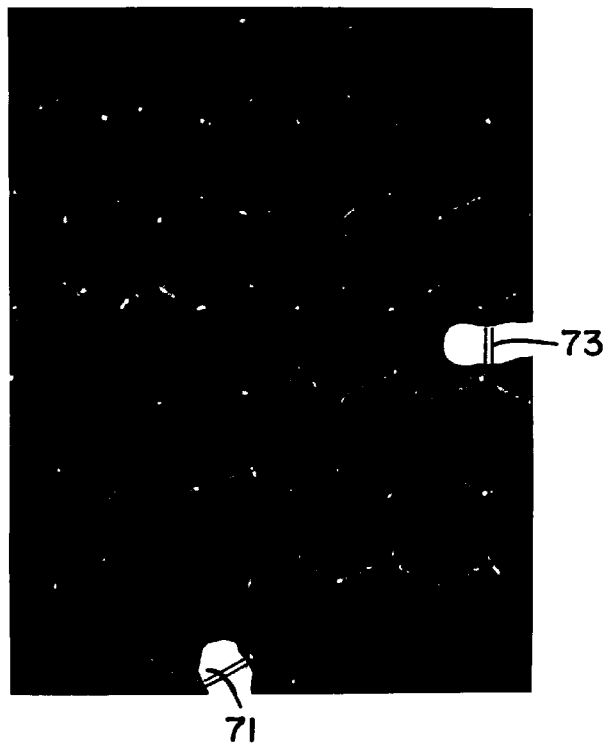
FIG. 6 representatively shows a suitable pattern of microcells which can be engraved onto the surface of the gravure roll.
Figure 6A:
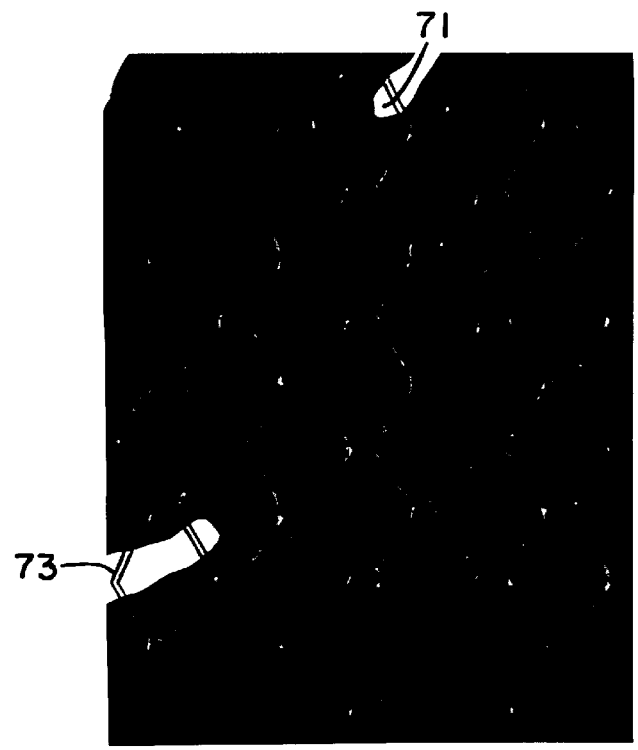
FIG. 6A representatively shows another suitable pattern of microcells which can be engraved onto the surface of the gravure roll.

The amount of adhesive applied to barrier tissue 56 depends upon the line-count of engraved cells per inch and the depth of the cells, measured in microns (micrometers). The cell volume is typically measured in cubic billion microns (CBM) per square inch. Particular embodiments of the gravure roll can have a cell line-count of about 1–1000 of cells per linear inch and can have a cell volume of about 0.1–250 CBM. Other embodiments can have a line-count about 16–600 cells per inch and about 1.9–174.5 CBM cell volume. In addition, the cells can be constructed in various suitable shapes, such as pyramidal, hexangular, trihelical, quadrangular or the like. The shown embodiment of gravure roll 80 incorporates hexangular cells, which have a six-sided shape, such as illustrated in FIGS. 6 and 6A. Optionally, the gravure roll may incorporate various types of quadrangular cells, such as normal, 45 degree quadrangular cells having a truncated pyramidal shape. Other gravure rolls may alternatively incorporate compressed, 30 degree cells or elongated, 60 degree cells.

As illustrated in FIG. 5, gravure roll 80 can be configured to transfer a predetermined add-on amount of adhesive along lateral side sections 79 of the roll surface. In the lateral side sections, the selected add-on amount can be provided by cells 71 which are arranged with a cell line-count of approximately 200 cells per linear inch and a volume capacity of approximately 14.3 CBM to form attachment regions 60 (FIG. 9) adjacent the edges of the absorbent cores, particularly the side edges of the cores. For example, with the hexangular cells representatively shown in FIG. 6, the individual cells 71 can have a cell depth of about 59–60 meters, and the separating wall 73 between the cells can have a wall thickness of about 5 micrometers.

In the medial section 78 of gravure roll 80, the selected add-on amount can be provided by cells which, for example, are arranged with a cell line count of approximately 200 cells per linear inch and a volume capacity of approximately 5.8 CBM to form attachment regions 60a (FIG. 9) adjacent the end edges of the absorbent cores, and supplemental attachment regions 86. For example, where the medial section of the gravure roll includes the hexangular cells representatively shown in FIG. 6A, the individual cells 71 can have a cell depth of about 20–21 micrometers, and the separating wall 73 between the cells can have a thickness of about 5–7 micrometers.

Gravure roll 80 can also be constructed and arranged to deliver a relatively higher or lower area concentration of adhesive along a medial section 78 of the outer surface of the gravure roll. In the shown embodiment, for example, the medial section of the gravure roll surface is configured with a line-count of approximately 200 cells per linear inch and a volume capacity approximately 5.8 CBM to deliver an adhesive add-on concentration that is lower than the adhesive concentration delivered by side sections 79.

With the shown embodiment, for example, the gravure roll is configured to provide for the generation of supplemental attachment regions 86 (FIG. 9) which can optionally bond barrier tissue 56 to a surface of absorbent cores 22. A representative supplemental attachment region 86 can include a series of discrete, spaced apart parallel stripes of adhesive placed onto discrete portions of barrier web 56 that overlie and contact absorbent core 22. The individual stripes are composed of continuous areas of adhesive, and these areas are substantially disconnected and spaced away from primary attachment regions 60.

In particular aspects of the invention, the engraved surface section of gravure roll 80 may be carried upon the outer cylindrical surface of a removable sleeve 75 to permit rapid changes in the desired adhesive printing pattern. The gravure roll sleeve may be removably attached to a shaft section 77 of the gravure roll, and the attachment can be provided by various suitable mechanisms, such as magnetic attachment, screws, latches, or the like.

Various mechanisms can be employed to deliver liquid adhesive onto gravure roll 80. For example, the liquid delivery mechanism can comprise a fountain roller immersed in an adhesive bath and having its outer cylindrical surface placed in direct contact with the outer surface of gravure roll 80. In this arrangement, a doctor blade is employed to scrape excess adhesive off of those portions of the gravure roll which include no depressions engraved therein.

Figure 7:
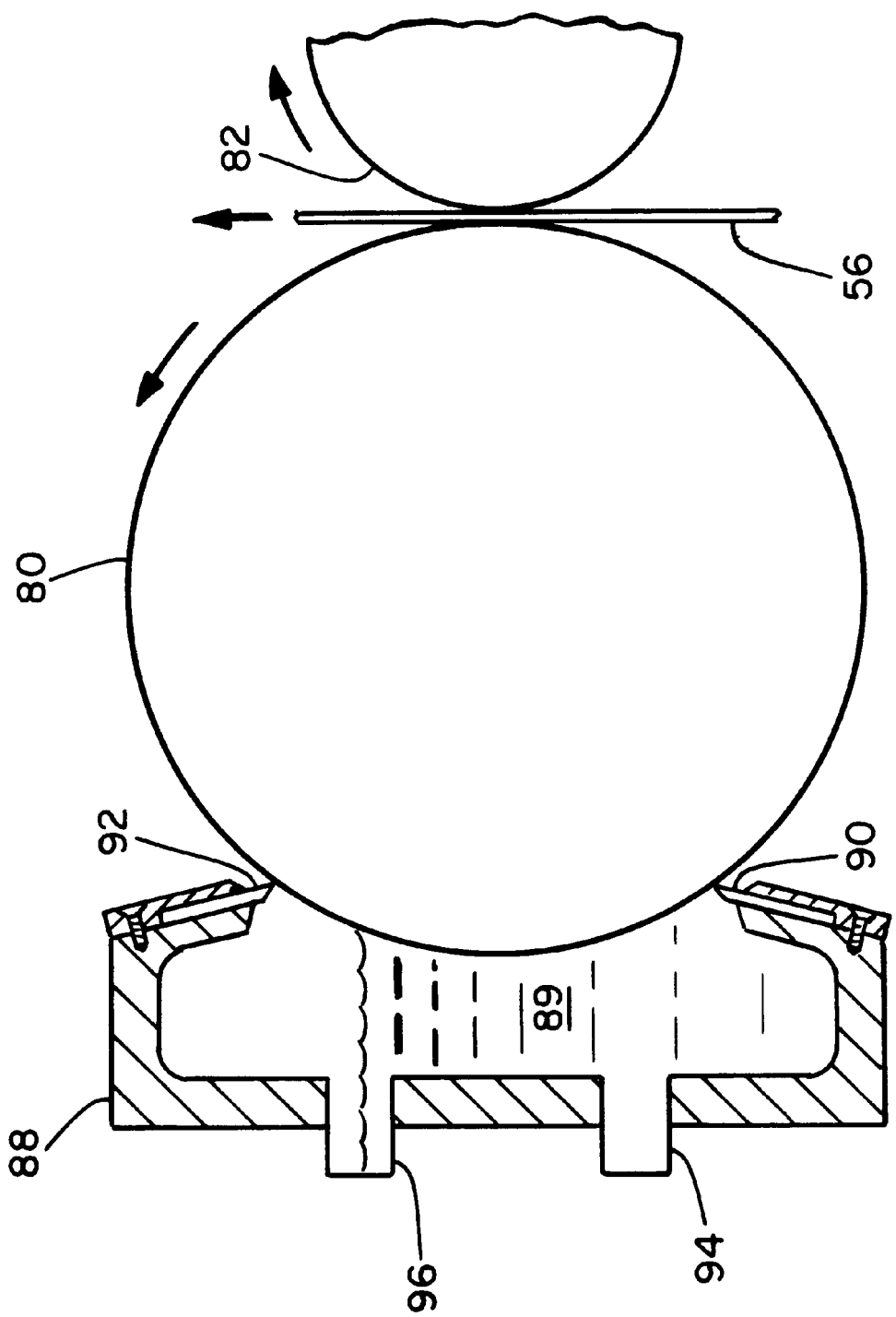
FIG. 7 representatively shows an enclosed chambered doctor blade applicator assembly.

The shown embodiment of the invention employs a delivery mechanism which is typically referred to as a chambered doctor applicator. This delivery system includes a closed fountain arrangement which deposits liquid adhesive 89 directly onto the surface of gravure roll 80. A cross-sectional view of the chambered doctor system is schematically shown in FIG. 7, and includes a reservoir chamber 88 in combination with a system of doctor blades 90 and 92. Chamber 88 includes an inlet supply conduit 94 and an outlet return conduit 96. The chamber further includes a side opening for receiving gravure roll 80 therein, and conventional liquid-resistent seals between the roll and chamber to hold the adhesive within the reservoir chamber. When chamber 88 is suitably filled with liquid adhesive, the surface of gravure roll 80 comes in direct contact with the adhesive. A primary doctor blade 90 is positioned at a bottom contact edge of chamber 88 and is employed to scrape excess adhesive off from the surface of gravure roll 80 while leaving adhesive filled in the minute depressions engraved on the surface of the gravure roll. A second, seal doctor blade 92 is positioned at a top contact edge of chamber 88 to prevent leakage of adhesive from the chamber.

It should be noted that the identification of the primary and seal doctor blades depends upon the direction of rotation of gravure roll 80. In particular, the primary doctor blade is the doctor blade positioned at the exit side of chamber 88 where the gravure roll rotation is moving the liquid-bearing, printing surface of the gravure roll out from the chamber. The seal doctor blade is the blade located at the entrance side of chamber 88 where the gravure roll rotation is transporting the printing surface into the chamber.

A selected liquid adhesive, such as a water soluble latex adhesive, is continuously pumped into the bottom center of reservoir chamber 88 through conduit 94, and the chamber is kept approximately ¾ full of adhesive. Two high-level drains positioned at the ¾ full level control the height and amount of adhesive within chamber 88. The drains exit excess adhesive for pumping back into a suitable glue reservoir. Adhesive chamber 88 moves in coordination with gravure roll 80, and the doctor blades are mounted on pivot brackets to facilitate clean-up, and to facilitate replacement of the doctor blades and replacement of the liquid seals needed to contain the liquid adhesive within the adhesive chamber. The pivot brackets also permit an adjustment of the alignments between the doctor blades and the gravure roll.

An adhesive suitable for use with the rotogravure printing system can have a viscosity of up to about 2,000 centipoise. For example, the adhesive may be a polyvinyl acetate based adhesive, such as National Starch 33-9157 and 33-9156, which are available from NATIONAL STARCH AND CHEMICAL CORPORATION, a business having offices at Bridgewater, N.J. Other suitable adhesives include latex based and polyvinyl alcohol based adhesives. The adhesive can optionally be selectively colored or otherwise marked to facilitate an optical or other detection of the printed adhesive pattern. This detection can then be employed to help control and register the location of the printed pattern relative to the positions of absorbent cores 22. In the shown embodiment, it is desireable to register adjacent to at least the side edges of the absorbent cores a printed pattern having a non-rectangular, curved or otherwise non-linear inside boundary. In more particular embodiments, it is desireable to register a printed pattern to substantially surround the entire perimeters of each of the individual absorbent cores.

With reference to FIG. 8, a representative impression roll 82 has a impression surface 93 composed of a resilient, compressible material, such as natural rubber, synthetic rubber, vinyl, photo polymer compositions or the like. FIG. 8A provides a view wherein the generally cylindrical impression surface has been unrolled and laid flat to more readily show the representative impression pattern.

The compressible surface of impression roll 82 has a relatively raised pattern formed thereon, and the raised pattern generally corresponds to the regions at which adhesive is intended to be transferred from gravure roll 80 onto barrier tissue 56. At those void areas 81 where it is desired to not transfer adhesive onto the barrier tissue, the surface of impression roll 82 is recessed away from gravure roll 80. Such recessed void areas 81 can be produced by forming desired pattern of depressions into the outer cylindrical surface of impression roll 82, and the patterned depressions can be produced by employing various techniques, such as machining, grinding, laser engraving or the like.

Figure 9:
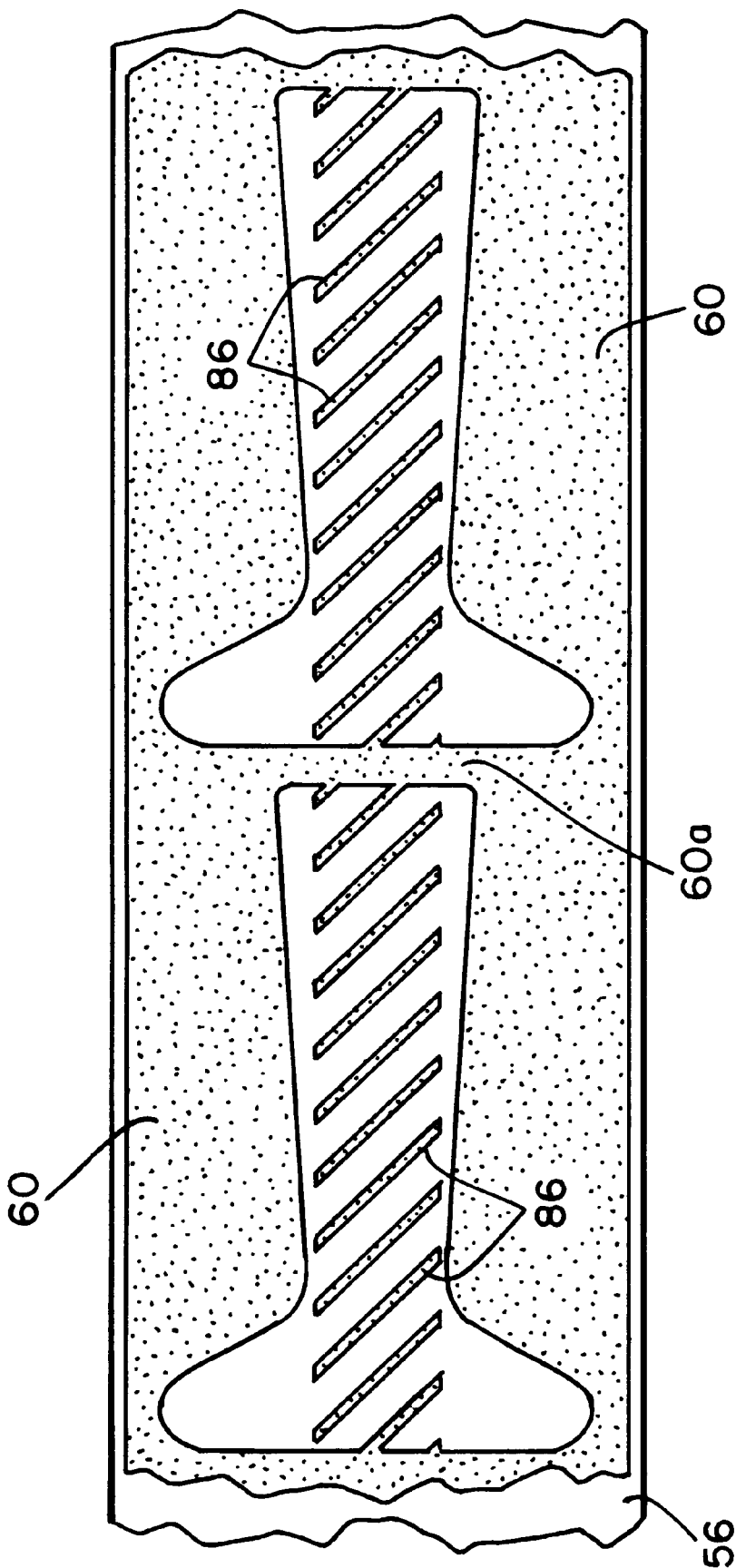
FIG. 9 shows a representative print pattern of adhesive applied onto a layer of web material.

In the shown embodiment of impression roll 82, the relatively raised pattern which includes two opposing, lateral side portions 95 and a medial section 97. Side patterns 95 are produced by selectively removing material from the surface of impression roll 82 along predetermined void areas 81 where adhesive is not intended for transfer onto the appointed substrate web. The resultant remaining surface areas are smooth and will provide for a nipping contact against the gravure roll 80. The side patterns are configured to produce lateral, side sections of primary attachment regions 60 (FIG. 9).

Medial pattern 97 of impression roll 82 is produced by removing material from selected areas of the surface of the impression roll to leave predetermined, remaining ridges or bars. The bars are relatively raised above the areas from which material has been removed from the impression roll surface. The remaining bar areas are smooth, and are configured to provided for a nipping contact against gravure roll 80 to produce supplementary attachment regions 86 as well as any cross-directional end sections of primary attachment regions 60.

The representatively shown embodiment of impression roll 82 is constructed to generate one complete print pattern for each revolution thereof. In addition, the gravure roll and the impression roll are constructed with different diameters so that all of the cells on the gravure roll are utilized during the adhesive printing process. In optional aspects of the invention, impression roll 82 may be constructed to generate a plurality of two or more complete print patterns for each revolution of the roll.

In particular aspects of the invention, impression roll 82 may have its outer surface carried upon a removable sleeve 87 which facilitates the changing of adhesive printing patterns. The outer cylindrical sleeve can be removably attached to a shaft section 85 of the impression roll, and the attachment can be provided by various suitable mechanisms, such as magnetic attachment screws, latches, or the like.

With reference again to FIG. 7, the backing or impression roll 82 is resiliently urged against gravure roll 80 along nip region 83 at a desired pressure, and the web of barrier tissue 56 is moved through the nip region between the gravure and impression rolls. The gravure roll can be hydraulically, mechanically, or pneumatically pressed against impression roll 80 to generate a desired level of nip pressure between the rolls. Typically, the pressure is within the range of about 10–500 pli (pounds per lineal inch of contact, as measured along the axial lengths of the contacting rolls). In the illustrated embodiment, gravure roll 80 is loaded against fixed stops by a conventional pneumatic cylinder mechanism. The fixed stops can be selectively adjustable to control the nip pressure and alignment between gravure roll 80 and impression roll 82.

The applied nip pressure generates a level of interference or "flat" between gravure roll 80 and impression roll 82, and the amount of flat can be controlled by varying the adjustable, mechanical stops. A typical flat value ranges from about 0 inch to about 1 inch. The nip pressure, the amount of flat, and the capillary action of the adhesive into the fibrous tissue cooperatively combine to transfer liquid adhesive from the minute depressions in gravure roll 80 onto barrier tissue 56 in a predetermined selected pattern. The quantities of liquid from the individual cells flow and merge together to form a continuous bond across the printed areas of the tissue.

A particular aspect of the invention includes a controlling means for regulating a selected registration between attachment region 60 and the series of absorbent cores 22. In the illustrated embodiment, the controlling means comprises a proximity switch and sensor with a marker flag attached to impression roll 82. The sensor generates a suitable signal, such as a mechanical, magnetic or electrical signal, or combination thereof, which indicates the position of each individual, periodic section of the printed adhesive pattern on barrier tissue 56.

The sensor signal can be sent to a computerized, automatic registration control system and employed as a reference marker. The relative location of the printed adhesive pattern on the barrier tissue can be determined visually by a machine operator. If machine operator notes that the print pattern is spaced away from the desired location on the tissue, and needs to be advanced or retarded to produce the correct registration, the operator enters an appropriate instruction into the registration system. The registration system then sends a signal to a conventional electronic drive system which is connected to the motor that drives the printer system composed of gravure roll 80 and impression roll 82. The drive system speeds up or slows down the motor, as needed to produce the desired registration between the adhesive printing pattern placed on the barrier tissue and the fluff pad or other absorbent body laid upon the barrier tissue.

The engraved roll can also be connected to a "Sunday" drive that slowly rotates the roll during machine stops. Such an arrangement can help keep the engraved roll surface wetted with liquid and prevent drying of the adhesive on the roll's surface. When the machine stops, the engraved roll can be pulled back away from the impression roll by air cylinders to allow it to rotate freely. The Sunday drive can, for example, be driven by a small AC motor through a separate gear train connected to the engraved roll.

The engraved roll shaft is attached to the main drive gear through a conventional one-way clutch to allow for the "Sunday" drive. At start-up, the "Sunday" drive is stopped or otherwise disengaged, and the air cylinders extend to position and press the engraved roll against the impression roll. Since the impression roll remains substantially stationary during the stop, registration and coordination of the impression roll with other machine components can be maintained. In particular, the impression roll can retain a relative rotational position which provides a desired registration that locates appointed sections of the printed adhesive pattern about and outwardly adjacent to the edge perimeters of absorbent cores 22.

When the engraved roll adhesive applicator switch is enabled ("ON"), the system can be configured to run the "Sunday" drive motor when the nip 83 is open, and can be configured to open and close the nip automatically. The machine can be threaded with the applicator switch disabled ("OFF"), but the machine will not go into the run mode. When the switch is in the disabled position, the system can be configured to stop the "Sunday" drive motor and to open the nip.

When the system is disabled, an impression roll nip test can also be conducted on the system to check whether the gravure and impression rolls are accurately aligned and parallel. For example, a layer of carbon paper and a layer of blank paper can be placed between the rolls to check the nip or amount of interference between the gravure and impression rolls. When the stopped rolls are brought together in nipping contact against the layers of paper, an imprint can be formed on the blank paper. The machine-direction widths of the transferred imprint can then be measured and the relative alignments of the gravure and impression rolls can be adjusted to generate a substantially uniform level of nipping and contact area along the axial length of the impression roll.

Figure 10:
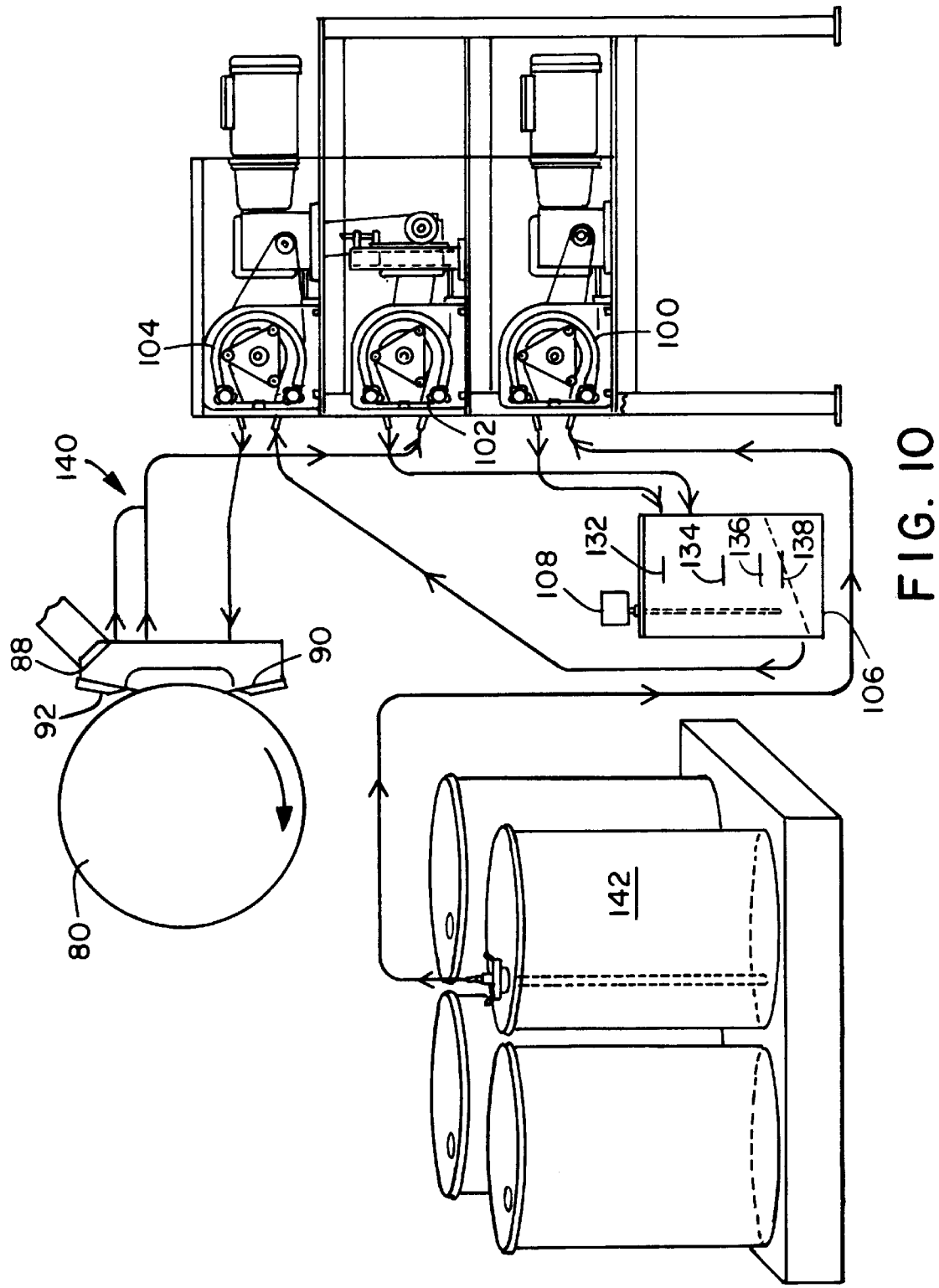
FIG. 10 representatively shows a system for delivering liquid adhesive to the adhesive applicator employed with the invention.

FIG. 10 schematically shows a representative system for providing a supply of liquid adhesive to the rotogravure printing system. The adhesive levels and flows are controlled by three separate peristaltic pumps (100, 102 and 104), and a reservoir 106 contains a level probe 108 with settings for four different levels. The pumps of the shown embodiment can, for example, be driven by 0.75 HP motors. The pumps work automatically when the fill level 134 is exposed and stop at the full level 132.

The chambered doctor applicator is continuously supplied by the supply pump 104. The adhesive is drawn off the bottom of reservoir 106 and is pumped to the bottom center of primary doctor blade 90. The surplus adhesive drains out of two upper level ports into a Y-connection 140 and is pumped back to the top of the reservoir 106 by return pump 102. The return pump is ordinarily geared to run faster than supply pump 104 to help prevent overflowing the chambered doctor applicator.

The reservoir level probe 108 has a check-drum level 136 that, when exposed, indicates that the supply drum 142 is empty. If the supply drum is not changed or otherwise replenished and the machine continues to run, a low-level 138 will be exposed and the machine will stop.

After the desired pattern of printed adhesive is applied to barrier tissue 56 an idler roll lifts the web up and away from the engraved roll 80, as illustrated in FIG. 4. With reference to FIG. 3, a printer conveyor 112, which can be controlled by a separate fixed drive, then moves the web of printed tissue to a fluff transfer screen 114. At the fluff transfer screen, the printed web of barrier tissue 56 is mated in the desired registration with the series of absorbent cores 22 and the associated web of forming tissue 50 coming off from the surface of forming drum 52. A fluff transfer conveyor 116 moves the mated, registered assembly from its position near forming drum 52 into the nip between a pair of debulker rolls 118. The debulker rolls are set and resiliently held at a selected gap, and operably compress together forming tissue 50, absorbent cores 22 and barrier tissue 56. This compression densifies the absorbent cores, and in the shown embodiment, helps to further set the adhesive bond between the forming and barrier tissues along attachment region 60.

Figure 11:
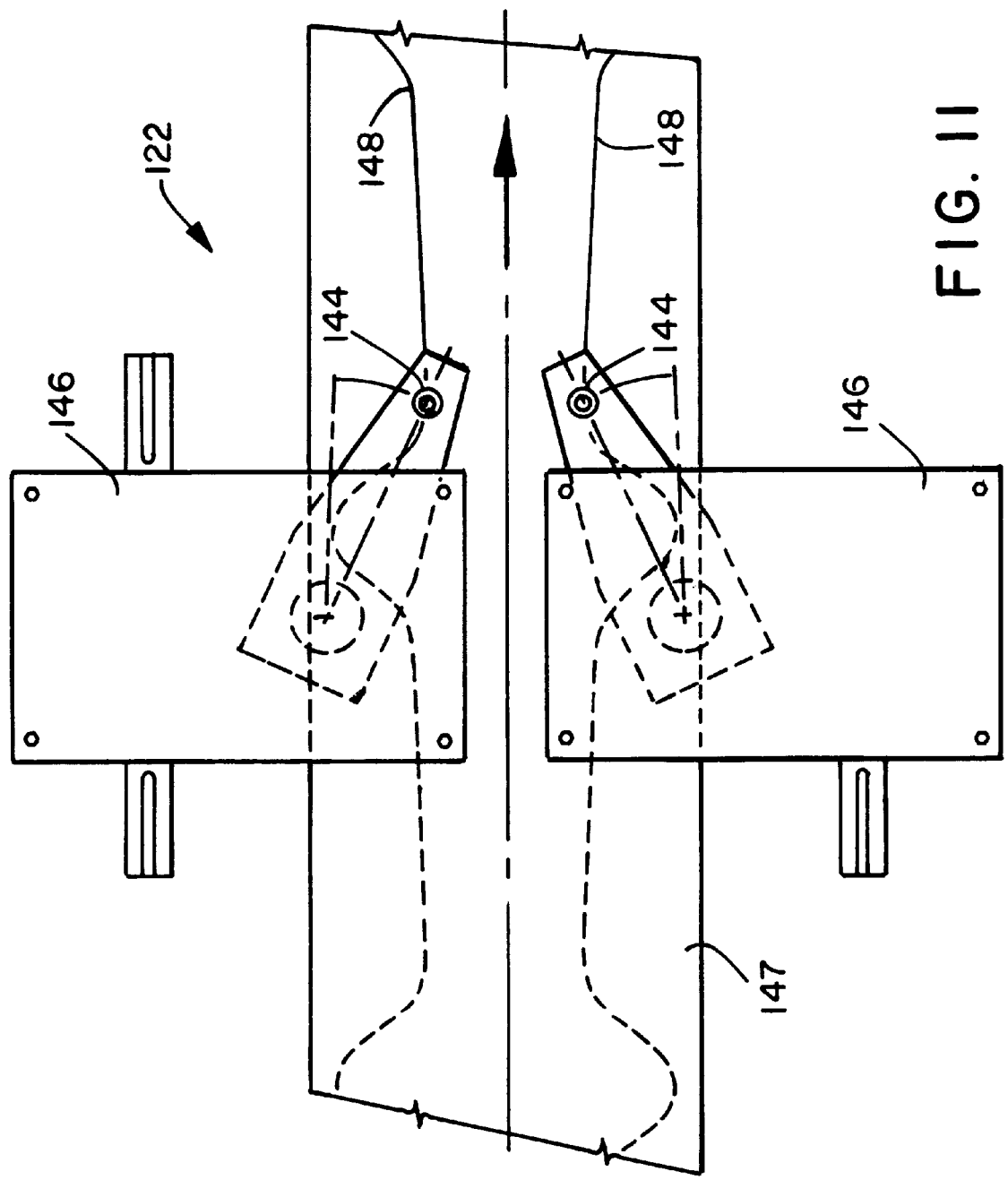
FIG. 11 representatively shows a device for cutting away selected portions of tissue wrap material.
Figure 12:
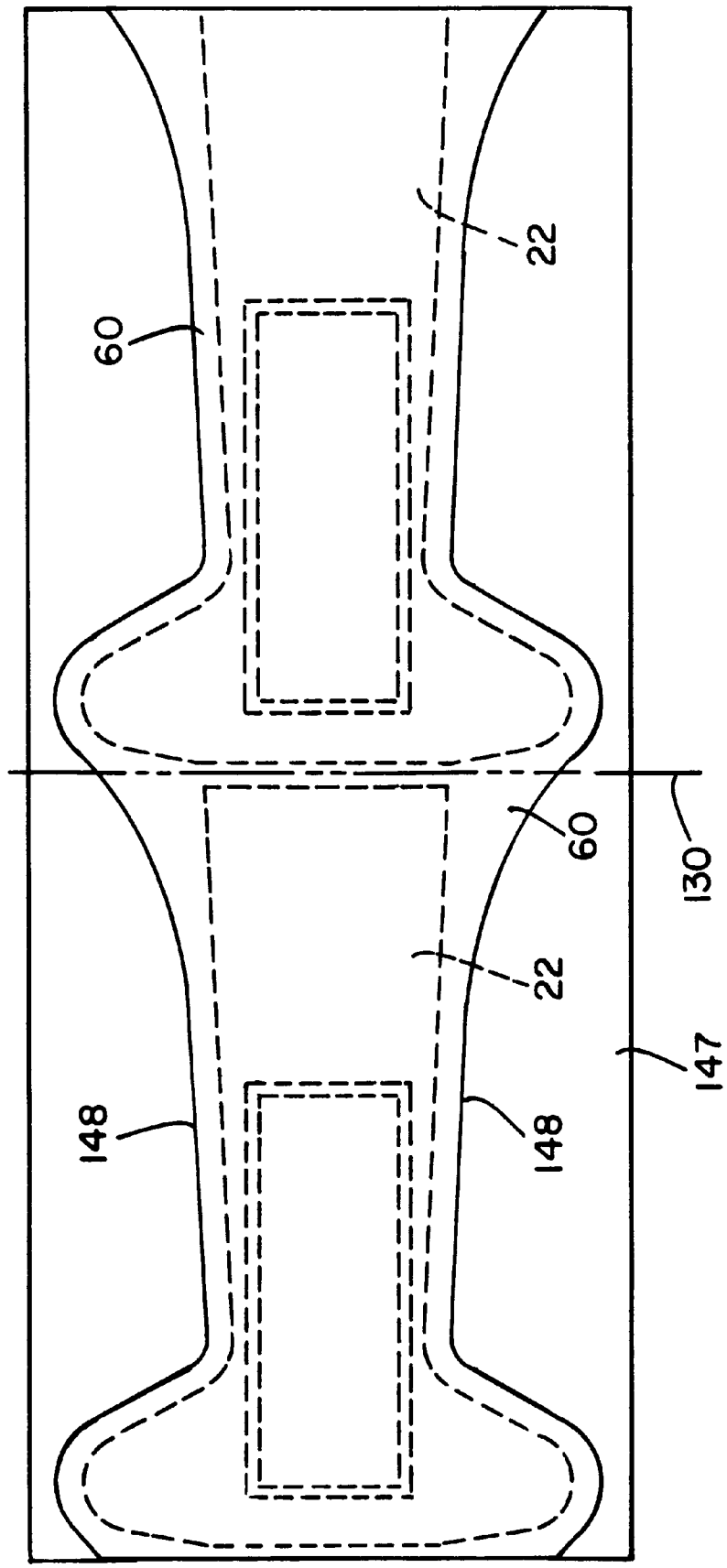
FIG. 12 shows a representative, cutting pattern generated along lateral side edges of a series of absorbent cores.

Upon leaving debulker rolls 118, a debulker conveyor 120 transports the debulked composite web 147 to a suitable separating means, such as cutting mechanism 62. In the embodiment representatively shown in FIG. 11, the cutting mechanism is provided by a conventional water cutter system 122 which cuts away selected sections of the composite web with high pressure jets of water. The water cutter jet nozzles 144 are placed at each of the lateral, cross-deckle side edges of the composite web composed of forming tissue 50, absorbent cores 22 and barrier tissue web 56. The water cutter nozzles are connected to conventional mechanisms, such as cam boxes 146, which oscillate the nozzles in a predetermined, periodic pattern substantially along the cross-deckle direction of the moving composite web to operably trace out symmetrically-opposed cutting paths 148, such as those representatively shown in FIG. 12. The water cutters separate away side regions of the composite web which are located adjacent to and outboard from the remaining, appointed attachment regions 60 that are intended to interconnect the top and bottom tissue layers covering the series of absorbent bodies 22.

Figure 3A:
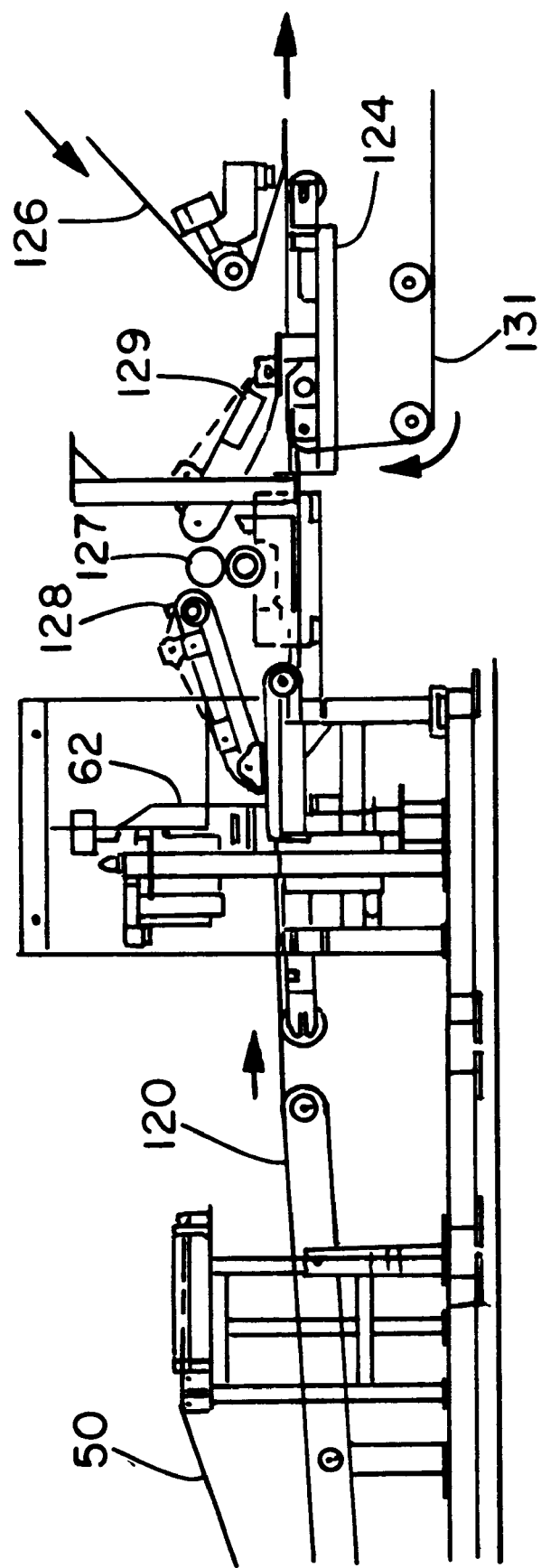
FIG. 3A representatively shows a schematic, side elevational view of further apparatus and processing steps that can be employed with the technique of the invention.

FIG. 3A representatively shows additional apparatus and processing steps that can continue from the system shown in FIG. 3. With reference to FIG. 3A, a water cutter conveyor 128 transports the resultant, trimmed composite web to a second cutting mechanism 127, such as provided by a rotary knife or other suitable cutting means. The second cutting mechanism separates the trimmed composite web along appointed dividing lines 130 (FIG. 13) to provide individual absorbent bodies 20 (e.g. FIG. 2). The representatively shown absorbent bodies include an absorbent core enveloped by a composite fluid permeable layer having a top, bodyside layer 28 composed of barrier tissue 56, and having a bottom, outerside layer 30 composed of forming tissue 50. The fluid permeable layer envelops and surrounds the absorbent core, and is sealed about the core perimeter, particularly along core side edges 42 and core end edges 44.

With reference again to the aspects of the invention illustrated in FIG. 3A, a conveyor 129 transports the separated absorbent bodies to a tacker station 124 where the absorbent bodies are sandwiched and operably attached between a web of topsheet material 131 and a web of outer cover or backsheet material 126. More particularly, the illustrated embodiment of conveyor 129 is configured in a conventional manner to position a series of absorbent bodies at predetermined, spaced-apart locations along the longitudinal, length dimension of topsheet web 131. The backsheet or outercover web 126 can then be directed by a suitable transporting mechanism to a position overlying both topsheet web 131 and absorbent bodies 20. Accordingly, the absorbent bodies are interposed between the topsheet and backsheet webs. In a conventional manner, a suitable attaching means, such as adhesive, bonds or otherwise holds together the constituent components of the composite assembly composed of topsheet web 131, absorbent bodies 20 and backsheet web 126.

Figure 14:
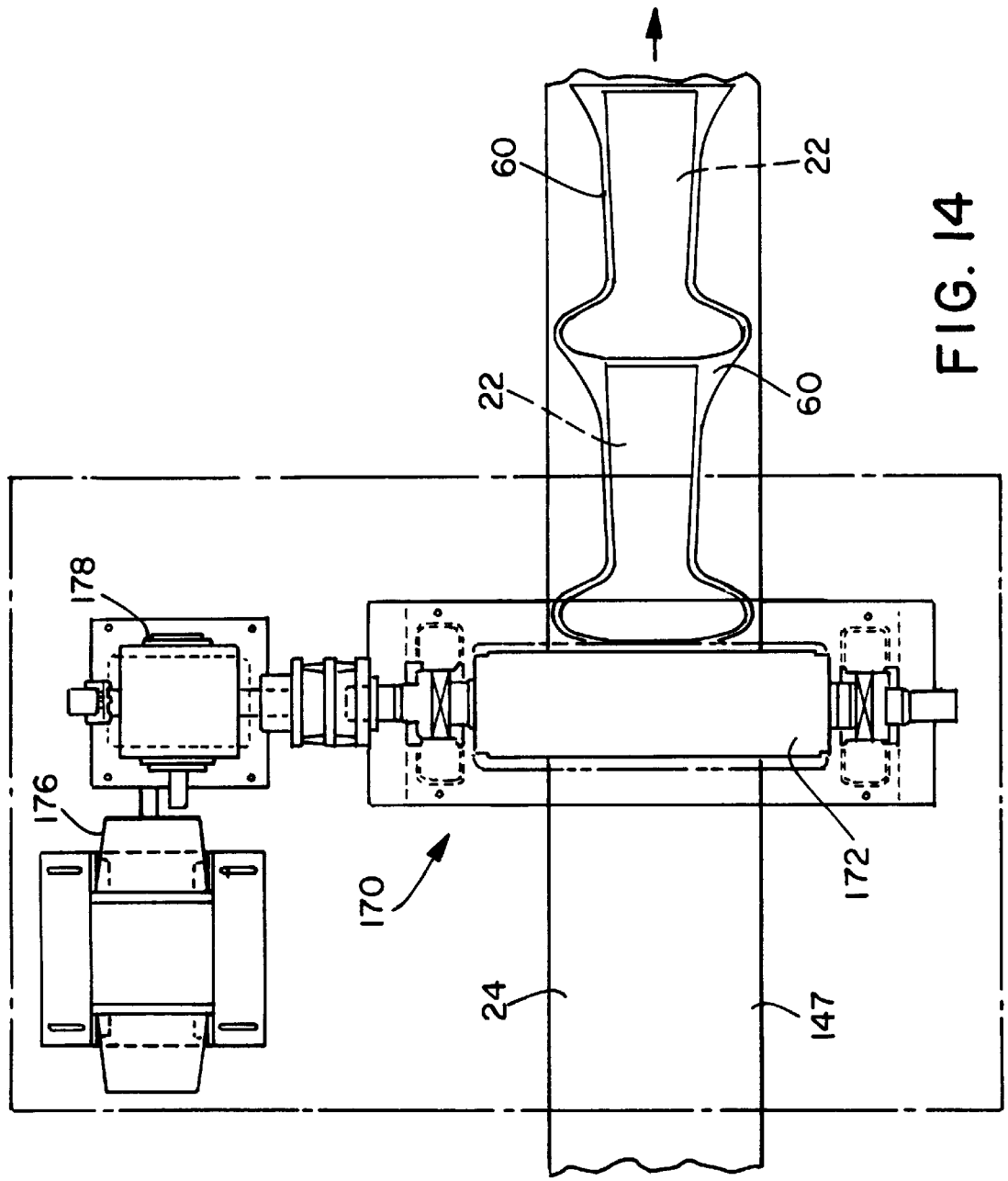
FIG. 14 representatively shows a top plan view of an embodiment of the invention configured to produce a thermal bonding pattern between layers of fluid permeable, thermally bondable material.

In alternative aspects of the invention, attachment region 60 can be produced with a thermal bonding mechanism, an ultra-sonic bonding system or the like. With reference to FIG. 14, for example, the invention can include a thermal bonding system 170 having a rotary anvil roll 172 and a heated pattern roll 174. The pattern roll can, for example, include a multiplicity of pins distributed in a selected pattern over the outer surface of the pattern roll. When composite web 147 passes through the nip region between the anvil and pattern rolls, the rolls produce thermally bonded attachment regions 60, which are arranged in a generally corresponding, selected pattern across the area of the composite web.

Figure 15:
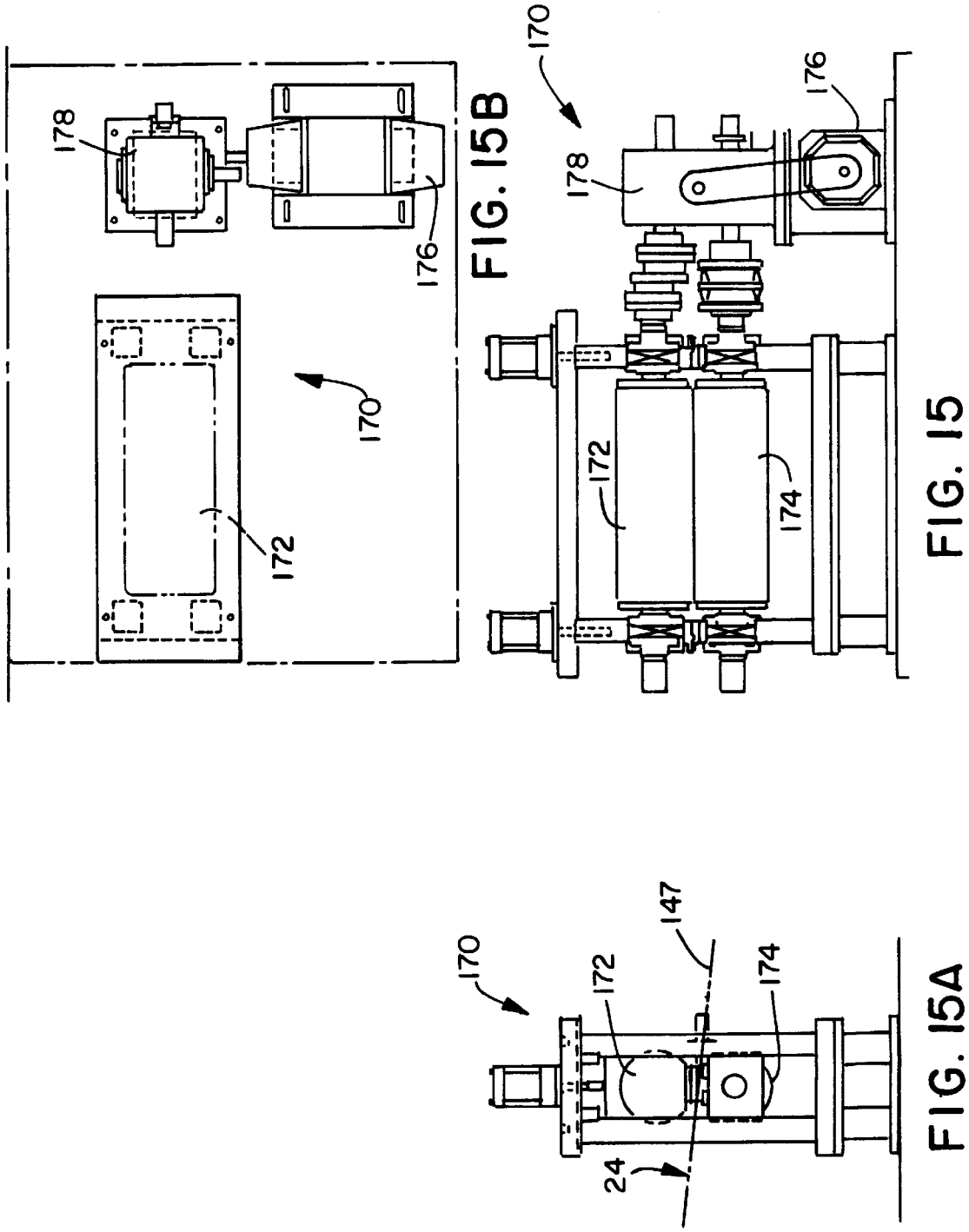
FIG. 15 representatively shows an end elevational view of a pair of thermal bonding rolls.

More detailed illustrations of thermal bonding system are representatively shown in FIGS. 15, 15A and 15B. The shown aspects of the thermal bonding system can advantageously include an electronic drive system 176 and drive motor 178 for maintaining desired speed and registration. The registration can, for example, be controlled in a manner similar to that employed with the adhesive printing system previously described herein. The rolls employed with the thermal bonding system can be heated by any suitable means, including but not limited to hot oil heating and induction heating.

The heated rolls create a bond by the contact between the anvil roll and the pins distributed over the surface of the pattern roll. The bonding can result from one or more of several mechanisms, such as conductive heat transfer, heat of deformation, flow bonding, diffusion bonding or melt bonding.

Figure 16:
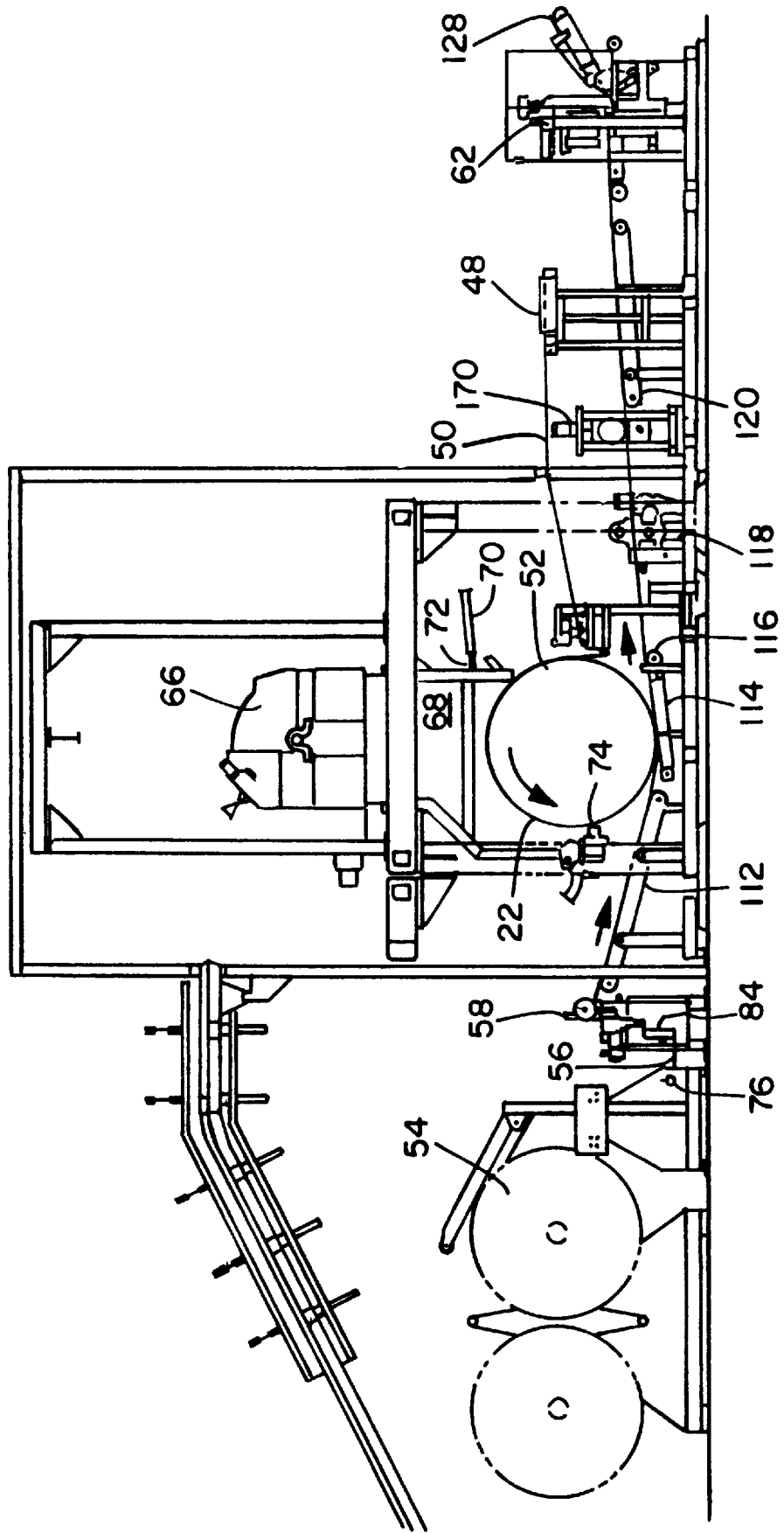
FIG. 16 representatively shows a schematic, side elevational view of the technique of the invention configured to employ a thermal bonding module.

FIG. 16 representatively shows an embodiment of the invention which incorporates a thermal bonding system 170. The thermal bonding system can, for example, be suitably positioned after debulker rolls 118 and before debulker conveyor 120. It should be readily appreciated that the additional apparatus and processing components illustrated in FIG. 3A can also be employed with the embodiment of the invention shown in FIG. 16.

When employing a thermal bonding system, either or both of forming tissue 50 and barrier tissue 56 include a proportion of heat-sealable material therein or combined therewith. Such heat-sealable material may, for example, include meltblown fibers composed of polyethylene, polypropylene, or the like. Alternatively, either or both of layers 50 and 56 of wrap material 24 may comprise a nonwoven fabric, such as a fabric composed of meltblown fibers. To provide adequate levels of bonding, the bonded regions of the layers have at least about 3 wt % of heat-sealable material contained or otherwise connected therewith. The bonded regions preferably include at least about 5 wt %, and more preferably include at least about 8 wt % of heat-sealable material.

In a particular aspect of the invention, a pair of phased, heated rolls have raised portions on the surfaces thereof, which correspond to the desired bonding pattern around the perimeter of the individual absorbent cores 22. A composite web, composed of a series of absorbent cores 22 sandwiched between a thermally bondable first web 50 and a thermally bondable second web 56, is moved through the nip region between the pair of heated and phased bonding rolls. The bonding rolls provide a temperature of about 100–400° F. at predetermined, raised regions of the bonding rolls and generate a pressure therebetween of about 100–1100 pli (pounds per linear inch). This pressure is determined with respect to a line representing the region of contact in the nip region between the bonding rolls. The heat and pressure are selected to operably generate attachment regions 60 which extend at least along side edges 42 of core 22. Preferably, the attachment regions also extend along end edges 44 of the core, and in the shown embodiment, the attachment regions extend around substantially the entire periphery 40 of the individual absorbent cores 22.

The thermal bonds may be configured and distributed in various suitable patterns. For example, the thermally bonded area may cover about 5–15% of the appointed attachment region, and the area size of the individual bonds can range from about 1 mm$^2$ to about 10 mm$^2$. Suitable distribution patterns for the bonds include regular or irregular patterns of separated geometric shapes, such as squares or circles, as well as regular or irregular wire-weave patterns. The illustrated embodiment can, for example, be constructed to produce individual thermal bonds measuring about 0.030 inch by 0.030 inch (about 0.0762 cm by 0.0762 cm) in size and having a spacing separation of about 0.040 inch (about 0.102 cm) between individual, adjacent bonds.

Having thus described the invention in rather full detail, it will be readily apparent to a person of ordinary skill that various changes and modifications can be made without departing from the spirit of the invention. All of such changes and modifications are contemplated as being within the scope of the present invention.

We claim:

1. An apparatus for enveloping a series of absorbent cores with a fluid permeable layer, comprising:

first web supplying means for providing a first layer of fluid permeable material;

depositing means for positioning a series of absorbent cores on said first layer, said absorbent cores defining a periphery thereof and including superabsorbent material therein;

second web supplying means for providing a second layer of fluid permeable material to sandwich said absorbent core between said first and second layers of material;

sealing means for securing said first layer to said second layer along an attachment a region thereof which is located adjacent to at least an opposed pair of curved side edge regions of said absorbent core, said attachment region constructed in a closed pattern;

separating means for removing selected curved regions of said first and second layers which are located adjacent to said attachment region and spaced from each of said side edge regions of said absorbent core, said separating means thereby leaving said closed pattern attachment region in a configuration which substantially prevents movement of superabsorbent material from said absorbent core through said attachment region when said absorbent core contains said at least about 30 wt % of said superabsorbent material therein; and means for sandwiching said absorbent core and said first and second webs between a web of topsheet material and a web of outer cover material.

2. An apparatus as recited in claim 1, further comprising controlling means for regulating a selected registration between said attachment region and said absorbent core.

3. An apparatus as recited in claim 1, wherein said sealing means is constructed to further secure said first layer to said second layer along an attachment region thereof which is located adjacent to at least said pair of side edge regions of said absorbent core and is also located adjacent a pair of longitudinal end regions of said absorbent core.

4. An apparatus as recited in claim 1, wherein said first web supplying means provides a first layer composed of a fibrous material.

5. An apparatus as recited in claim 1, wherein said second web supplying means provides a second layer composed of a fibrous material.

6. An apparatus as recited in claim 1, wherein said second web supplying means is constructed to provide a second layer which is composed of a fibrous material and has a lower average pore size value than said first layer.

7. An apparatus as recited in claim 6, wherein said second layer has a average pore size value of not more than about 60 micrometers.

8. An apparatus as recited in claim 1, wherein said depositing means is constructed to position an absorbent core which includes a pair of laterally positioned, outwardly concave, side edge regions.

9. An apparatus as recited in claim 1, wherein sealing means is constructed to secure said first layer to said second layer along an extending, flange-shaped attachment region.

10. An apparatus as recited in claim 1, wherein said sealing means is constructed to substantially avoid attaching said first layer or second layer to side regions of said absorbent core.

11. An apparatus as recited in claim 1, wherein said sealing means is constructed to secure said first layer to said second layer with a substantially closed pattern of adhesive.

12. An apparatus as recited in claim 11, wherein said sealing means comprises a system for printing an adhesive onto said attachment region.

13. An apparatus as recited in claim 12, wherein said system for printing adhesive provides said adhesive at a cell line-count within the range of about 16–600 cells per inch and a cell volume within the range of about 1.9–174.5 CBM.

14. An apparatus as recited in claim 13, wherein said system for printing adhesive provides said adhesive at a cell line-count of about 200 cells per inch.

15. An apparatus as recited in claim 1, wherein said first web supplying means provides a first layer of air permeable web material which is thermally bondable; said second web supplying means provides a separate, second layer of fluid permeable web material which is thermally bondable; and said sealing means comprises a system for thermally bonding said first layer to said second layer along said attachment region with a substantially closed bonding pattern.

16. An apparatus as recited in claim 1, wherein said sealing means is arranged to construct said attachment region in a closed pattern which substantially prevents movement of superabsorbent material from said absorbent core through said attachment region when said absorbent core contains at least about 40 wt % of superabsorbent material therein.

17. An apparatus as recited in claim 1, wherein said sealing means is arranged to construct said attachment region in a closed pattern which substantially prevents movement of superabsorbent material from said absorbent core through said attachment region when said absorbent core contains at least about 50 wt % of superabsorbent material therein.

18. A method for enveloping a series of absorbent cores with a fluid permeable layer, comprising the steps of:

supplying a first layer of fluid permeable web material;

positioning a series of discrete cores of absorbent material on said first layer, each of said absorbent cores defining a periphery thereof and including superabsorbent material therein;

supplying a separate, second layer of fluid permeable web material to sandwich said absorbent cores between said first and second layers of material;

securing said first layer to said second layer along a selected attachment region thereof which is located adjacent to at least an opposed pair of curved side edge regions of said absorbent cores, said attachment region constructed in a closed pattern;

removing selected curved regions of said first and second layers which are spaced from each of said curved side edge regions of said absorbent cores and located adjacent to said attachment region, said removing step thereby leaving said closed pattern attachment region in a construction which substantially prevents movement of superabsorbent material from said absorbent core through said attachment region when said absorbent core contains said at least about 30 wt % of said superabsorbent material therein; and sandwiching said absorbent core and said first and second webs between a web of topsheet material and a web of outer cover material.

19. A method as recited in claim 18, wherein said securing step is arranged to secure said first layer to said second layer along an attachment region thereof which is located adjacent to at least said pair of side edge regions of said absorbent core and is also located adjacent a pair of longitudinal end regions of said absorbent core.

20. A method as recited in claim 18, wherein said securing step is arranged to secure said attachment region in a closed pattern which substantially prevents movement of superabsorbent material from said absorbent core through said attachment region when said absorbent core contains at least about 40 wt % of superabsorbent material therein.

21. A method as recited in claim 18, wherein said securing step is arranged to secure said attachment region in a closed pattern which substantially prevents movement of superabsorbent material from said absorbent core through said attachment region when said absorbent core contains at least about 50 wt % of superabsorbent material therein.

22. A method as recited in claim 18, wherein said securing step is arranged to secure said attachment region in said closed pattern with adhesive, said adhesive provided at a cell line-count within the range of about 16–600 cells per inch and a cell volume within the range of about 1.9–174.5 CBM.

23. An method as recited in claim 22, wherein said securing step is arranged to secure said attachment region in said closed pattern with adhesive provided at a cell line-count of about 200 cells per inch.

* * * * *